US011160685B1

(12) United States Patent
Homer

(10) Patent No.: US 11,160,685 B1
(45) Date of Patent: Nov. 2, 2021

(54) LASER SYSTEMS AND METHODS FOR ALTERATION OF EYE COLOR

(71) Applicant: STROMA MEDICAL CORPORATION, Irvine, CA (US)

(72) Inventor: Gregg Homer, Irvine, CA (US)

(73) Assignee: Stroma Medical Corporation, Irvine, CA (US)

( * ) Notice: Subject to any disclaimer, the term of this patent is extended or adjusted under 35 U.S.C. 154(b) by 0 days.

(21) Appl. No.: 17/238,070

(22) Filed: Apr. 22, 2021

Related U.S. Application Data

(60) Provisional application No. 63/165,683, filed on Mar. 24, 2021.

(51) Int. Cl.
*A61F 9/008* (2006.01)

(52) U.S. Cl.
CPC ...... *A61F 9/00802* (2013.01); *A61F 2009/00846* (2013.01); *A61F 2009/00876* (2013.01); *A61F 2009/00897* (2013.01)

(58) Field of Classification Search
None
See application file for complete search history.

(56) References Cited

U.S. PATENT DOCUMENTS

| | | | |
|---|---|---|---|
| 5,549,596 A * | 8/1996 | Latina | A61F 9/008 606/4 |
| 6,306,127 B2 | 10/2001 | Homer | |
| 6,881,249 B2 * | 4/2005 | Anderson | A61K 8/0241 106/31.03 |
| 7,036,516 B1 * | 5/2006 | Dees | A61B 18/203 128/898 |
| 8,206,379 B2 | 6/2012 | Homer | |
| 10,744,034 B2 | 8/2020 | Homer | |
| 2009/0163898 A1 * | 6/2009 | Gertner | A61B 3/14 606/4 |
| 2020/0054489 A1 * | 2/2020 | Thyzel | A61F 9/00802 |

FOREIGN PATENT DOCUMENTS

| | | |
|---|---|---|
| WO | 2001003569 | 8/2001 |
| WO | 2002062259 | 8/2002 |

OTHER PUBLICATIONS

"Iris pigmentation and pigmented lesions: an ultrastructural study," Trans Am Ophthalmol Soc 1988;86:581-687. PMID: 2979031; PMCID: PMC1298824.

"Image-Based Modeling of the Human Eye" IEEE Transactions On Visualization And Computer Graphics, vol. 15, No. 5, Sep./Oct. 2009.

(Continued)

*Primary Examiner* — Shirley X Jian
(74) *Attorney, Agent, or Firm* — Perkins Coie LLP

(57) ABSTRACT

A method for altering an eye color of a patient with a color alteration procedure is disclosed that may include determining a laser power to deliver to stromal pigment in an iris of the eye of the patient by at least retrieving a set of laser criteria for delivery of an exposure less than 100 times a maximum permissible exposure that causes elimination of at least a portion of the stromal pigment. A laser system may be set to deliver laser light at the laser power which is less than the set of laser criteria and the laser light may be delivered with the laser system.

26 Claims, 7 Drawing Sheets

(56) References Cited

OTHER PUBLICATIONS

"Don't it make my blue eyes brown: heterochromia and other abnormalities of the iris" Eye (2012) 26, 29-50; Published online Oct. 7, 2011; Presented at the Oxford Ophthalmological Congress 2010.

"Scheimpflug Camera-Based Stereo-Digital Image Correlation for Full-Field 3D Deformation Measurement," Hindawi Journal of Sensors, vol. 2019, Article ID 5391827, 11 pages (Oct. 10, 2019), https://doi.org/10.1155/2019/539182.

"Introduction To OCT" http://obel.ee.uwa.edu.au/research/fundamentals/introduction-oct/ Date unknown, downloaded Nov. 9, 2020.

"American National Standard for Safe Use of Lasers," ANSI Z136.1-2007, ISBN-13: 978-0-912035.65-9 & ISBN-10: 0-912035-65-X, (May 2007).

"Development of Close Proximity Wireless Technology with Integrated On-Chip Antenna," https://www.renesas.com/us/en/about/press-room/development-close-proximity-wireless-technology-integrated-chip-antenna, Jun. 29, 2010.

\* cited by examiner

LASER SYSTEMS AND METHODS FOR ALTERATION OF EYE COLOR

RELATED APPLICATION(S)

This application claims priority to and the benefit of U.S. Provisional Application No. 63/165,683, filed Mar. 24, 2021, titled "Laser Systems And Methods For Alteration Of Eye Color," which is hereby incorporated by reference.

FIELD OF THE INVENTION

The invention relates to delivering laser light of particular power levels and in a geometry suitable for medical procedures related to changing an eye color of a patient.

BACKGROUND

The use of lasers for eye surgery has increased recently. However, while laser eye surgery is a known option for the correction of one or more vision problems such as near-sightedness (myopia), farsightedness (hyperopia), and astigmatism, little interest has been shown to operations other than those for correcting vision problems. For example, advancements in laser eye surgeries have focused on operations through which a laser may reshape a patient's cornea and have ignored other parts of a patient's eye and procedures therefor.

SUMMARY

In view of this, methods and systems are discussed herein for delivering laser light to an iris of a patient. In particular, the methods and systems discussed herein are for performing an eye color changing procedure through this delivery of laser light. For example, changing a person's eye color may be performed by delivering laser light to portions of the eye that are responsible for giving the eye its color (e.g., the iris).

To achieve this effect, the methods and systems must overcome several technical hurdles. For example, in conventional laser eye surgeries (e.g., those aiming to correct vision), the amount of laser power utilized may be somewhat arbitrary and/or variable. If such systems were applied to the iris (e.g., for eye color changing procedures), this may lead to inconsistent results and in some cases potential damage the iris. Similar challenges exist because conventional approaches to eye surgery use a one-size-fits-all approach in which the eye is treated as a homogenous structure. Such an approach overlooks the local differences in the eye that affect the outcome of an eye color change procedure.

In view of these technical hurdles, the methods and systems discussed herein deliver laser light at a laser power based on calculated minimum radiative exposure (MRE) values at the iris of the eye to achieve efficacy and maximum permissible exposure (MPE) value at the fundus of the eye to avoid unwanted injury. Also discussed are diagnostic capabilities including temperature monitoring during the procedure, accurate rangefinding to ensure the proper delivery of light to the targeted structures, and iris mapping to provide to provide tailored power delivery to specific regions of the eye.

These methods and systems provide numerous advantages over conventional methods for obtaining eye color changes such as colored contact lenses, corneal staining and tattooing, and prosthetic iris implants. For example, with colored contact lenses, such problems include: an unnatural appearance if blue or green contact lenses are used to make brown eyes appear blue or green; only a temporary color change; poor tolerance by about 50% of patients; risk of eye infection, corneal abrasion, and other eye disorders; and poor night vision because the clear center does not dilate with the pupil of the eye. Recent literature has also suggested that the pigments used in colored contact lenses may be released into the body after prolonged use. Other solutions are available, including corneal pigmentation and colored iris implants. Problems with corneal pigmentation include the same unnatural appearance and poor night vision as colored contact lenses, plus the added risks associated with an invasive surgical procedure. Problems with colored iris implants include all of the problems associated with corneal pigmentation, plus poor tolerance by 50% of patients within 24 hours and over 90% of patients within 1 year, and colored iris implants are far more surgically invasive, often resulting in glaucoma and loss of visual acuity. Neither corneal pigmentation nor colored iris implants have been approved for cosmetic use.

The methods and systems overcome these shortcomings of conventional systems by delivering laser power based on the MPE to perform a safe and effective eye color changing procedure. Such delivery has advantages in that the settings of the laser system are directed to an outcome rather than sent to arbitrary parameters which may or may not result in the proper delivery of laser power to the eye. To ensure that the laser power is delivered accurately, novel methods of rangefinding are disclosed. Such methods may include micron level resolution in laser focus locations in the eye to deliver the desired laser power exactly where needed. Also disclosed are methods of staged applications of laser treatment to provide an optimized and tailored treatment to the patient. Such staged applications may overcome variations in stromal pigment absorption coefficients and anterior iris surface topography (e.g., tilt, folds, and crypts). Such staged applications may also benefit from determination of elements of the patient's immune response as this may have a direct effect on the procedure and thus the laser system parameters used.

In order to facilitate the altering of the eye color of the patient, the system may determine the laser power to be delivered to stromal pigment in the iris of the patient's eye, with the laser power having an upper bound of some fraction of the MPE. Once this determination is made, the laser system may be set to deliver the needed laser power. Also, the system may determine an optimized spot size (i.e., spot diameter defined at $1/x^2$) of the laser at the location of the stromal pigment. Such determination of the optimized spot size may then be used by the system to determine the needed laser power for the procedure.

In some aspects, a method for altering a patient's eye color may include determining the laser power to deliver to stromal pigment in the iris of the eye. The determination may be performed by the system retrieving a set of laser criteria for delivery of an exposure less than 100 times the MPE but will still cause elimination of at least a portion of the stromal pigment thereby changing the eye color. The method may then include setting the laser system to deliver the laser light at the power level, which is less than the set of laser criteria, and delivering the laser light with the laser system.

In a related aspect, a method for altering a patient's eye color may include determining a spot size for laser light to be delivered to stromal pigment in the iris of the eye. The determination may be done by the system at least retrieving a set of laser criteria that results in delivery of laser light having a spot size of 4-70 μm to a stromal pigment of an iris of the patient. With these criteria, the laser power delivered by the laser light at the spot size is sufficient to cause elimination of at least a portion of the stromal pigment. The method may then include setting the laser system to deliver the laser light at the spot size and delivering the laser light with the laser system.

In another interrelated aspect, a tangible, non-transitory, machine-readable medium storing instructions that, when executed by a data processing apparatus, causes the data processing apparatus to perform operations comprising those of any of the above embodiments.

In yet another interrelated aspect, a system may include one or more processors and memory storing instructions that, when executed by the processors, cause the processors to effectuate operations comprising those of any of the above embodiments.

Various other aspects, features, and advantages of the invention will be apparent through the detailed description of the invention and the drawings attached hereto. It is also to be understood that both the foregoing general description and the following detailed description are examples and not restrictive of the scope of the invention. As used in the specification and in the claims, the singular forms of "a," "an," and "the" include plural referents unless the context clearly dictates otherwise. In addition, as used in the specification and the claims, the term "or" means "and/or" unless the context clearly dictates otherwise. Additionally, as used in the specification "a portion," refers to a part of, or the entirety of (i.e., the entire portion), a given item (e.g., data) unless the context clearly dictates otherwise.

DETAILED DESCRIPTION OF THE DRAWINGS

In the following description, for the purposes of explanation, numerous specific details are set forth in order to provide a thorough understanding of the embodiments of the invention. It will be appreciated, however, by those having skill in the art, that the embodiments of the invention may be practiced without these specific details or with an equivalent arrangement. In other cases, well-known structures and devices are shown in block diagram form in order to avoid unnecessarily obscuring the embodiments of the invention.

INTRODUCTION

The present disclosure provides improved methods and systems for facilitating medical procedures to change the eye color of a patient. Such medical procedures may involve delivering laser power to portions of the eye such that a biological reaction occurs that alters the pigment structure of the eye and thereby changes its color. Determining the proper laser power to use based on the needs of the procedure, safety to the patient, variations from patient to patient, and variations from treatment to treatment (for a multistage treatment) may be critical to a successful outcome.

Figure 1:
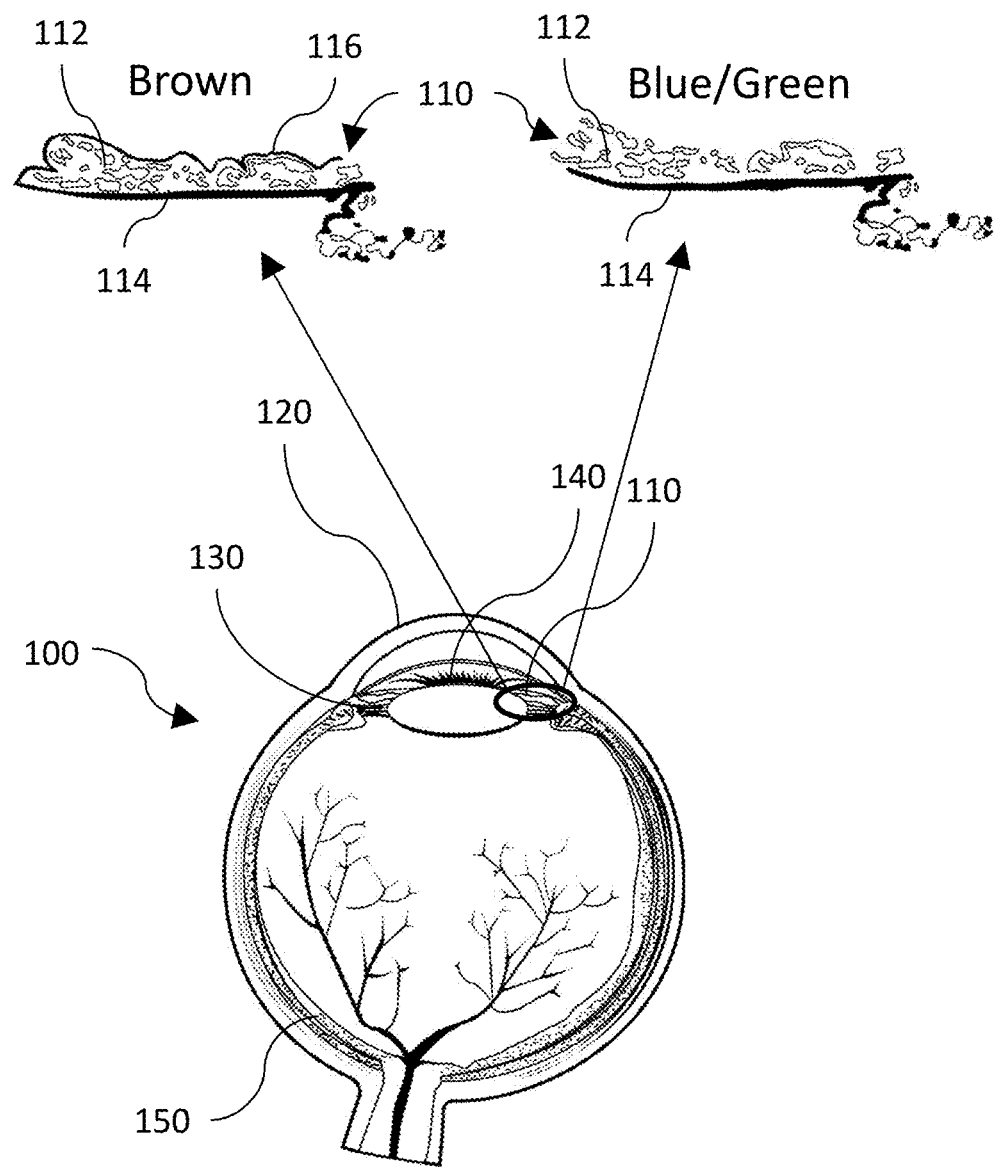
FIG. 1 shows a simplified diagram of the eye and iris.

Before describing the color alteration procedure, which is applicable to many embodiments of the present disclosure, a brief overview of the anatomy of the eye is provided. As shown in FIG. 1, eye 100 is composed of several anatomical structures, a few of which are discussed below. Central to the present disclosure, the iris 110 is responsible for the color of the eye. Other portions of the eye include, for example, cornea 120, lens 130, pupil 140, and retina 150. While care should be taken to avoid damaging any part of the eye, in the practice of laser safety, special precautions should be taken to avoid directing unwanted laser light through the pupil and into the lens as this part of the eye naturally focuses light onto the retina. Such focusing of already intense laser light may result in injury to the retinal nerves.

Shown in the insets above the eye are two examples of irises. The example on the left is a depiction of an iris 110 in a person with brown eyes. The example on the right depicts an iris 110 of a person with blue or green eyes. The perceived color is due to light reaching the eye being separated into its component wavelengths by stromal fibers in the middle region of the iris—referred to as the iris stroma 112. The separation is similar to the separation exhibited when light passes through a prism. In both cases, the iris has a posterior surface 114 that contains a fairly thick (several cells deep) layer of pigmentation that primarily absorbs visible light wavelengths longer than blue or green. However, in the example on the left for a person with brown eyes, there is an additional anterior surface that contains brown pigment, herein referred to as "stromal pigment" 116. The brown stromal pigment gives the eye a brown color. Eyes without the stromal pigment reflect mostly blue or green light as described above, giving the eye a blue or green color.

A brief summary of a color alteration procedure as referenced herein is provided. Laser light may be delivered to the stromal pigment to cause an increase in temperature of the stromal pigment. This process may be repeated several times to repeatedly raise and lower the temperature of the stromal pigment. This raising and lowering of the temperature causes the body to deploy macrophages (part of the body's natural immune response) to the stromal layer. These macrophages then remove a portion of the stromal pigment responsible for giving the eye its brown color. Repeated procedures may be performed to provide varying degrees of color change to make the eye appear a deeper blue/green. The delivery of the laser light may be in a scanning pattern (e.g., a spiral pattern surrounding the pupil or a raster pattern avoiding the pupil) to deliver the treatment to the entire iris.

Figure 2:
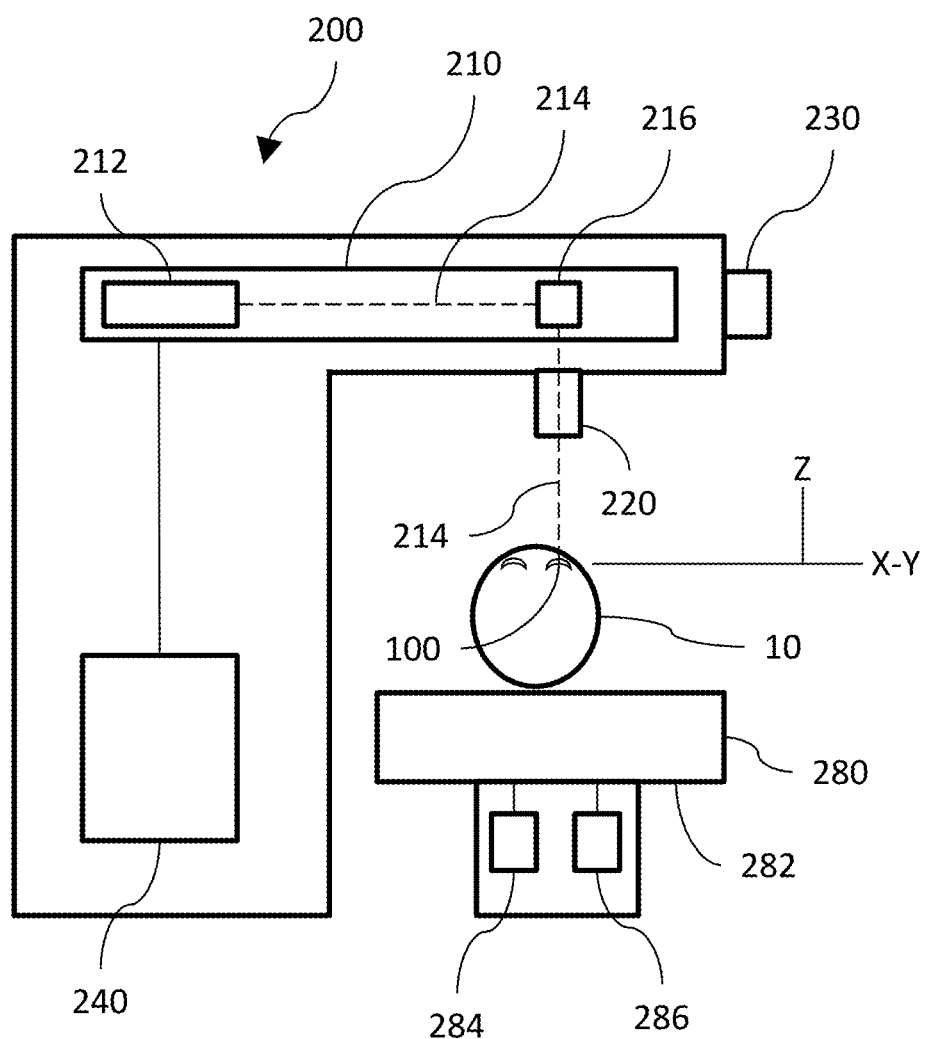
FIG. 2 shows a simplified diagram of a laser system and patient positioning system in accordance with one or more embodiments.

FIG. 2 shows a simplified diagram of a laser system and patient positioning system in accordance with one or more embodiments. One embodiment of the overall system 200 may include the laser system 210 and a patient positioning system 280. The head of patient 10 (with eyes 100) is shown supported by the patient positioning system in a location suitable for the color alteration procedure. The laser system may include the laser head 212 which provides laser light 214. The laser head may include components to generate laser light at varying wavelengths, for example, at 1064 nm or 532 nm (Nd:YLF or Nd:YAG). Exemplary pulse widths may be in the 5-300 ns with repetition rates of 5-300 kHz and an $M^2 \leq 1.2$.

The laser head may include an energy source (aka a pump or pump source), a gain medium, and two or more mirrors that form an optical resonator. Exemplary energy sources include: electrical discharges; flashlamps; arc lamps; output from another laser; and chemical reactions. Exemplary gain media include: liquids (e.g., dyes comprising chemical solvents and chemical dyes); gases (e.g., carbon dioxide, argon, krypton, and helium-neon); solids (e.g., crystals and glasses, such as yttrium-aluminum garnet, yttrium lithium fluoride, sapphire, titanium-sapphire, lithium strontium aluminum fluoride, yttrium lithium fluoride, neodymium glass, and erbium glass), which may be doped with an impurity (e.g., chromium, neodymium, erbium, or titanium ions) and may be pumped by flashlamps or output from another laser; and semiconductors, with uniform or differing dopant distribution (e.g., laser diode).

Embodiments of the laser head may include an optical frequency multiplier (e.g., a frequency doubler and sum-frequency generator), where the laser output frequency is increased by passing it through a non-linear crystal or other material. The benefit of an optical frequency multiplier is that it increases the range of frequencies/wavelengths available from a given gain medium. The non-linear material may be inserted into the optical resonator for one-step frequency multiplication, or the fundamental (i.e. non-multiplied) output beam may be passed through the non-linear material after leaving the optical resonator for two-step frequency multiplication. Exemplary non-linear materials for frequency doubling may include: lithium niobate, lithium tantalate, potassium titanyl phosphate, or lithium triborate. Two-step frequency tripling is typically performed by frequency doubling a fraction of the fundamental output beam in a first step. The doubled fraction of the fundamental beam and the non-doubled remainder of the fundamental beam are then coupled into a second non-linear frequency tripling material in a second step for sum-frequency mixing. Exemplary non-linear materials for frequency tripling may include potassium dihydrogen phosphate.

One combination of gain medium and optical frequency multiplier is Nd:YAG with a frequency doubler. The natural harmonic of a laser beam generated by an Nd:YAG gain medium is a wavelength of 1,064 nm, which is then halved to 532 nm by the frequency doubler. This wavelength may be utilized as: (a) it falls within the visible light spectrum (i.e., green), thereby passing through the clear cornea with little or no absorption; (b) it has a high absorption coefficient in stromal pigment, thereby effecting selective photothermolysis in the anterior stromal pigment of the iris; and (c) the wavelength is relatively short, thereby limiting the depth of penetration and avoiding unwanted damage to the IPE. Any other combination of gain media and optical frequency multiplication that meets these three criteria is also may also be implemented in some embodiments.

Laser pulse widths may be in the nanosecond range (i.e., from below 1 nanosecond to 1 microsecond) and the pulse repetition rate may be in the kilohertz range (i.e., from below 1 kHz to 1 MHz). Some embodiments may have a pulse width between 5 ns and 300 ns, which may provide improved pigment denaturation. Q-switching may be utilized as a preferred pulsing method as it tends to be optimally suited to the nanosecond pulse width. Some embodiments include active Q-switching with a modulator device.

As used herein, "laser" means any device capable of generating a beam of optical radiation, whether in the infrared, visible light, or ultraviolet light spectrum. The term "laser" is not intended to restrict: (a) the properties of the optical radiation in terms of monochromaticity or coherence (e.g., divergence or directionality); (b) whether the radiation is continuous or pulsed; (c) if pulsed, the specific pulse width (e.g., zeptosecond attosecond, femtosecond, picosecond, nanosecond, millisecond, or microsecond); (d) the repetition rate; (e) the laser power; (f) the wavelength or frequency of the beam; (g) the number of wavelengths or frequencies, i.e., single v. multi-frequency output (e.g., intense pulsed light); (h) the number of beams, i.e., single v. multiple beams (e.g., splitting of a single beam or generating multiple beams from multiple lasers); or (i) the gain medium.

As used herein, "laser power" may mean either $W/cm^2$ or $J/cm^2$, depending on the context—as they are related by the exposure time. The MPE may be expressed in either of those units. For example, MPE may include the maximum level of laser radiation to which a fundus may be exposed without hazardous effects or biological changes in the eye.

Accordingly, when the specification refers to a laser power in terms of an MPE, the exact value of the laser power depends on, among other things, the beam spot size, pulse duration, or wavelength, and whether the laser is pulsed or continuous, etc. Thus, the determination of the MPE provides a basis for the skilled person to determine the laser power in the various embodiments disclosed herein.

As used herein, when referring to "reducing," "lowering," "less," etc., in the context of adjusting the laser power, this is understood to mean that the laser system may reduce the laser power from a current value to a lower (nonzero) value while still delivering laser light in some respect. These definitions also include redirecting the laser beam (e.g., to a beam dump) such that the delivered laser power is reduced. These definitions also include turning off the laser system (i.e., lowering the laser power to zero). Lastly, reducing the laser power may also include performing any of the above in a repetitive fashion thereby lowering the duty cycle of the laser beam or performing any combination of the above in an intermittent fashion.

Galvos systems 216 (also referred to as the x-y beam guidance system) may be included in the laser system and may include adjustable mirrors to provide a means of delivering the laser light to various locations on an X-Y plane (typically the plane of the iris where the laser light usually focused). Further implementations of the laser system may include, for example rangefinders and/or optical tracking systems, which may include cameras to determine an X-Y deviation of the center of the eye relative to the optical axis of the laser system.

In some embodiments, the x-y beam guidance system may scan the beam spot about the iris surface. The scanning parameters may include the size, shape, and position of the target region, the line and spot separation between each beam spot, and the predetermined scan pattern. The computer imaging software may determine the size, shape, and position of the target region based upon iris images captured by the x-y imaging system and transmitted to the computer for processing. Once processed, the size, shape, and position data may be transmitted to the scanning program to drive the x-y beam guidance system. New iris images may be captured at predetermined intervals and transmitted to the computer for processing throughout the procedure. Captured images are compared, and if they indicate a change in iris position, the computer imaging software calculates the x-y deltas and transmits the shift coordinates to the scanning program, which in turn executes the shift in the scanning position. In some procedures, a topical cholinergic agonist such as pilocarpine hydrochloride ophthalmic solution 2% (e.g., Isopto Carpine 2% from Alcon, Geneva, Switzerland) may be instilled in the target eye prior to treatment to constrict the pupil, flatten out the iris surface, and mitigate changes in the iris size and shape during the procedure. The line and spot separation between each beam spot may be predetermined and programmed into the scanning program prior to treatment. In some cases, the spot and line separation place each beam spot tangent to the others throughout the target region. The scan pattern may be raster (including slow-x/fast-y and slow-y/fast-x), spiral (including limbus to pupil and pupil to limbus), vector, and Lissajous scans.

In one embodiment, the x-y beam guidance system may scan the beam spot about the iris surface by means of controlled deflection of the laser beam. Embodiments utilizing beam steering in two dimensions may drive the beam spot about the two-dimensional surface of the iris. Beam motion may be periodic (e.g., as in barcode scanners and resonant galvanometer scanners) or freely addressable (e.g., as in servo-controlled galvanometer scanners). Exemplary beam steering in two dimensions may include: rotating one mirror along two axes (e.g., one mirror scans in one dimension along one row and then shifts to scan in one dimension along an adjacent); and reflecting the laser beam onto two closely spaced mirrors mounted on orthogonal axes.

There are numerous methods for controlled beam deflection, both mechanical and non-mechanical. Exemplary non-mechanical methods may include: steerable electro-evanescent optical refractor or SEEOR; electro-optical beam modulation; and acousto-optic beam deflection. Exemplary mechanical methods may include: nanopositioning using a piezo-translation stage; the micro-electromechanical system or MEMS controllable microlens array; and controlled deflection devices. Mechanically controlled deflection devices may include: motion controllers (e.g., motors, galvanometers, piezoelectric actuators, and magnetostrictive actuators); optical elements (e.g., mirrors, lenses, and prisms), affixed to motion controllers; and driver boards (aka servos) or similar devices to manage the motion controllers. The optical elements may have a variety of sizes, thicknesses, surface qualities, shapes, and optical coatings, the selection of which depends upon the beam diameter, wavelength, power, target region size and shape, and speed requirements. Some embodiments may utilize optical elements that are flat or polygonal mirrors. An embodiment of the motion controller may include a galvanometer, including a rotor and stator (to manage torque efficiency) and a position detector (PD) (to manage system performance). An exemplary PD may include one or more illumination diodes, masks, and photodetectors. Driver boards may be analog or digital. Scan motion control might also comprise one or more rotary encoders and control electronics that provide the suitable electric current to the motion controller to achieve a desired angle or phase. The installed scanning program disclosed above may be configured to collect measured scan and target region data.

The x-y beam guidance system may apply the laser spot to all or any portion of the anterior iris surface. Treated fractions of the anterior iris surface may include the following (which are inclusive and do not take into account any spared tissue due to line and/or spot separations): greater than ¼; greater than 30%; greater than ¼; greater than ½; and greater than ¾.

The system can include one or types of rangefinding apparatuses to measure the Z distance from a reference point to the target (e.g., the iris surface). As used herein, the Z direction is taken to be the vertical direction, perpendicular to the X-Y plane (e.g., the iris surface). A component referred to herein as optical exit 220 may be provided to allow the exiting of laser light to reach the eye. Optical exit 220 may include windows, lenses (e.g., dichroic lenses), mirrors, shutters, or other optical components. In some implementations, the system may include platform control 230, which may be configured to provide coarse adjustment (manually or automatic computer-controlled) in the X, Y, or Z directions. The platform control 230 may also be configured to perform fine adjustments similar to the above, with such fine adjustments implemented by computer control. Also included in some implementations are control computer and power supplies, depicted by element 240 in FIG. 1. Alternatively, control computers or electronics and some or all of the needed power supplies need not be contained in the system 200 as depicted in FIG. 1, but may be distributed in other locations or networked to be operatively connected to the laser system. Examples of rangefinding apparatuses may include systems that perform triangulation, time-of-flight measurements, etc., with one specific example being an optical coherence tomography system. Further discussion of rangefinding and/or tracking apparatuses is provide throughout the application, such as in the discussion of FIG. 4A.

Patient positioning system 280 is shown in the simplified diagram as containing patient support 282. Examples of patient support may include a flatbed, recliner, couch, head or neck brace, etc. Control of the patient positioning system may be realized by, for example, X-Y actuator 284 and/or Z actuator 286, which may be configured to move the patient in the respective directions for optimal alignment with the delivered laser light.

Included in the present disclosure are methods for the improved delivery of laser light for performing the above-described color alteration procedure. One way to deliver a consistent and clinically safe amount of laser light that is still effective for performing the color alteration procedure may include the system determining laser criteria in terms of this safe amount.

The laser settings used for treatment as described in the present disclosure may be determined by the system based on a number of parameters. One parameter may be the maximum permissible radiative exposure limit at the fundus plane of the eye ("MPE"). The MPE is a safety parameter to protect the retina from injury. A second parameter may be the minimum required radiative exposure at the iris plane of the eye ("MRE"). The MRE is an efficacy parameter to ensure that a threshold radiative exposure value is achieved for stromal pigment elimination.

The MPE may be obtained according to international safety standards. Examples of such standards include (a) American National Standard for Ophthalmics—Light Hazard Protection for Ophthalmic Instruments (ANSI Z80.36-2021), published by the American Nation al Standards Institute (New York, N.Y., USA) in 2021, and (b) Safety of Laser Products—Part 1: Equipment Classification and Requirements (IEC 60825-1), published by the International Electrotechnical Commission (Geneva, Switzerland) in 2014.

In some implementations, the wavelength (A) of the laser radiation may be between 305 nm and 1350 nm, inclusive, and the single pulse width (t) of the laser radiation may be between 100 fs and 5000 s, inclusive. To provide one example, which may change based on updating of the above-described standards, within these A and t ranges the MPE may be calculated as follows:
(a) If 100 fs<t≤10 ps; and
　(i) $\lambda=700$ nm, then MPE=8.0 mJ/cm$^2$.
　(ii) $\lambda \neq 700$ nm, then MPE=8.0 mJ/cm$^2$ divided R($\lambda$), where R($\lambda$) is defined as the thermal hazard weighting function for a given A in Appendix 1.
(b) If 10 ps<t<3 μs; and
　(i) $\lambda=700$ nm, then MPE=20.0 mJ/cm$^2$
　(ii) $\lambda \neq 700$ nm, then MPE=20.0 mJ/cm$^2$ divided by R($\lambda$).
(c) If 3 μs≤t<5000 s, then MPE is given by the following Equation (1):

$$\frac{\left(\frac{10}{d_r} \cdot t^{0.75}\right) \frac{J}{cm^2}}{R(\lambda)}$$

where
　t is the single pulse width (in seconds);
　$d_r$ is the minimum retinal image diameter (in mm) of the laser beam in the standard eye; and
　if $d_r \geq d_r$(max), then $d_r=d_r$(max), where
　　if 3 μs≤t<0.25 s, then $d_r$(max)=3.4·t$^{0.5}$ mm;
　　if t≥0.25 s, then $d_r$(max)=1.7 mm; and
　　if $d_r$(max)≤0.03 mm, $d_r$=0.03 mm.

The MRE is the minimum radiative exposure value capable of denaturing the pigment granules (melanosomes) within the pigment cells (melanocytes) located primarily along the anterior surface of the iris of the eye and secondarily and at lesser density within the stromal fibers of the iris of the eye. Denaturation of these pigment granules occurs at or about the temperature at which microbubbles first occur on the surfaces of the granules. These microbubbles typically occur at approximately 120° C. These microbubbles need not be maintained for a long duration or recreated multiple times. A single exposure may be sufficient to induce denaturation of the granule. Once a critical mass of these granules is denatured within a given cell, the cell will die off, signaling macrophages residing in and about the iris to digest the cell and remove it through the vasculature of the iris.

Real-time detection of the melanosome surface microbubbles may be achieved by the system monitoring the anterior iris surface optically or acoustically during treatment. One embodiment of an optical microbubble monitoring system may include a video microscope using a standard 40× microscope objective through which fast flash photographs may be taken by a high-speed image device (such as the 4 Quik E ICCD nanosecond high-speed camera from Stanford Computer Optics, Berkeley, CAS, USA), a frame grabber (such as the Cyton-CXP4 from BitFlow, Woburn, Mass., USA), and a 3-5 ns flash illumination source (such as the VSL-337ND-S Pulsed Nitrogen Laser from Spectra-Physics, Santa Clara, Calif., USA). Another example of an optical microbubble monitoring system captures the increased light reflection from the generated bubble-water interface using confocal imaging to a photomultiplier (such as the H7827-001 photosensor module from Hamamatsu, Hamamatsu City, Japan). The system may then record the output data using a transient recorder (such as the TR40-16 bit-3U from Licel GmbH, Berlin, Germany) and transfer the recorded data to a computer (such as the TPC-2230 from NI, Austin, Tex., USA) for processing and analysis. Similarly, the system may include an electron microscopy system configured to perform electron microscopy on the iris during a treatment session (e.g., real-time and in-situ). For example, an electron microscopy system (such as the Quantax 70 (Bruker AXS Microanalysis GmbH, Berlin, Germany) may be configured to image and detect microbubbles as described above.

One embodiment of an acoustic microbubble monitoring system may include a hydrophone (such as the HFO-690 optical fiber hydrophone from Onda, Sunnyvale, Calif., USA). Again, the output data may be recorded using a transient recorder (such as the TR40-16 bit-3U from Licel GmbH, Berlin, Germany) and transferred to a computer (such as the TPC-2230 from NI, Austin, Tex., USA) for processing and analysis.

The descriptions of exemplary laser powers that may be delivered are used to cause biological actions that result in the desired alteration in eye color. Accordingly, in some implementations, the laser power may be sufficient to cause a concurrent temperature change in the stroma pigment, which then causes macrophages in the iris to remove at least a portion of the stromal pigment. In this way, monitoring of the iris temperature may be performed by the system to determine the MRE (e.g., detecting the exposure at which microbubbles begin to form). In some specific embodiments, the laser power may be at least 20 times the maximum permissible exposure such that a reduction of the laser power to below 20 times the maximum permissible exposure does not cause loosening denaturing of the stromal pigment and the resultant change in eye color. To facilitate delivery of laser power to cause sufficient temperature changes in the stromal pigment, some methods may include determining, with a temperature sensor, a temperature of at least a portion of the iris that contains stromal pigment. In some embodiments, the temperature sensor may be of a type non-invasive to the iris. Examples of temperature sensors may include more direct temperature sensors such as passive infrared detectors that image the eye or more indirect temperature sensors utilizing acoustical monitoring that detects acoustical signals (sounds or pressure waves) indicative of microbubble formation (e.g., as expected to occur around 120° C. and thus an approximation of the temperature crossing that threshold). Heat transfer from within the iris may manifest itself as local heating at the surface of the eye. Computer modeling of predicted or a priori heat patterns may be associated with the measured heat pattern to derive a heat pattern at the activated stromal pigment. For example, with an implementation that utilizes an infrared imaging system, the received infrared radiation may be converted by the imaging system, or a connected computer receiving data from such, to a local temperature in the iris. Such a conversion may be performed using a blackbody approximation or other similar methods.

One factor complicating ascertainment of the MRE is that it may vary from one melanosome to the next based upon the absorption coefficient between the wavelength of the radiative energy and the color value and/or density of the melanosome. If the MRE is too low for a given melanosome, no microbubbles will form, the melanosome will not be denatured, and its melanocyte will not be digested and eliminated. Conversely, if the MRE is too high for a given melanosome, too much heat will be generated within the melanocyte, ablating the melanocytes and causing them to burst, releasing the melanosomes into the anterior chamber of the eye, potentially causing inflammation in the adjacent tissues and its associated adverse conditions. The MRE for a given melanosome must therefore be appropriate for each melanosome.

By way of example, a 532 nm wavelength may be generated by the laser system to treat an iris with melanosomes having three color values/densities: tan, medium brown, and dark brown. The MRE required to denature the dark brown melanosomes will be lower than the MRE required to denature the tan and medium brown melanosomes (because the absorption coefficient between the wavelength and the dark brown color value/density is higher). The MRE required to denature the medium brown melanosomes will be higher than the MRE required to denature the dark brown melanosomes (because the absorption coefficient between the wavelength and the medium brown color value/density is lower), and the MRE required to denature the medium brown melanosomes will be lower than the MRE required to treat the tan melanosomes (because the absorption coefficient between the wavelength and the medium brown color value/density is higher). And the MRE required to denature the tan melanosomes will be higher than the MRE required to denature the medium and dark brown melanosomes (because the absorption coefficient between the wavelength and the tan color value/density is lower). Denaturation of the stromal melanosomes of this iris will therefore require three different MREs.

Real-time detection of the melanosome surface microbubbles will inform each MRE in the above example. In one embodiment, the initial radiant exposure value is too low to induce microbubbles but is gradually increased until microbubbles are first detected. Let us call this "MRE I." The entire iris may then be treated using MRE I. This treatment will denature the dark brown melanosomes, and their melanocytes will be digested and eliminated over the next 3-4 weeks. At 4 weeks, the treatment protocol may be repeated. Because most or all of the dark brown melanosomes are eliminated, the first microbubbles will be detected at a higher radiant exposure value. Let us call this "MRE II." The entire iris may then be treated using MRE II. This treatment will denature the medium brown melanosomes, and their melanocytes will be digested and eliminated over the next 3-4 weeks. At 4 weeks, the treatment protocol may be repeated. Because most or all of the medium brown melanosomes are eliminated, the first microbubbles will be detected at a higher radiant exposure value. Let us call this "MRE III." The entire iris may then be treated using MRE III. This treatment will denature the tan melanosomes, and their melanocytes will be digested and eliminated over the next 3-4 weeks. If stromal melanocytes remain on the anterior iris surface, treatment may be repeated using MRE III.

If melanocytes remain within the iris stroma, they will absorb the backscattered blue or green light, making the grey of the stroma fibers more visible, producing a grey-blue or grey-green perceived iris color. Many patients are satisfied with this perceived color because the grey increases the color value of the eye, making them appear brighter. For those patients who prefer a more saturated blue or green color hue, the treatment may be repeated at the MRE III value, but with the laser beam waist shifted from the anterior iris surface to the interior stroma. This treatment will denature the melanocytes remaining within the iris stroma and eliminate or reduce the absorption of the backscattered blue or green light.

Highly sensitive methods and devices should be used for real-time microbubble detection. If detection is not sufficiently sensitive, and the microbubbles are not detected when they first appear, the radiant energy will be too high, causing ablation of the melanocytes and inflammation of anterior chamber tissues. The radiative exposure value for two laser iris procedures, "argon laser trabeculoplasty" ("ALT") and "selective laser trabeculoplasty" ("SLT"), is established by increasing the radiative energy until "champaign bubbles" are visible on the trabecular meshwork ("TM"), and then reduced slightly. These champaign bubbles are substantially larger than microbubbles, and they occur at a higher radiative exposure value. Because the ALT and SLT procedures are limited to scattered clusters of melanocytes originating from the iris pigment epithelium and lodged in the TM, delivery of an excessive radiative exposure value and ablation of these clusters is unlikely to release a sufficient quantity of melanosomes to cause serious inflammation or injury to the eye. Here, however, an excessive radiative exposure value and ablation of the stromal melanocytes can cause severe inflammation and could in theory cause long-term injury.

In one implementation, the following exemplary MRE ranges are given for each of the following melanosome color values/densities, where $\lambda=532$ nm, $t=11.475$ ns, the pulse repetition rate (prr)=135 kHz, and the incidence angle of the beam to the iris plane $(\theta_i)=0°$:

| MRE | Color Value/Density | MRE Range (mJ/cm$^2$) |
|---|---|---|
| MRE I | Dark brown | 250-400 |
| MRE II | Medium brown | 550-650 |
| MRE III | Tan | 750-850 |

The above MRE ranges are specific to the laser radiation parameters described above, but may vary with changes in these parameters. The methods for determining the MPE, however, take the relevant parameters into account. Therefore, the MRE ranges will necessarily take these parameters into account if they are expressed as multiples of the MPE.

Using $R(\lambda)=2.10$ as the weighting factor given in Appendix 1 for $\lambda=532$ nm and $t=11.475$ ns, the MPE is 9.52 mJ/cm$^2$ (i.e., 20 mJ/cm$^2$/2.10). The MPE for the parameters used in the Exemplary Embodiment is therefore approximately 9.52 mJ/cm$^2$, and the MREs can be expressed by the following MPE multiples:

| MRE | MRE Range (mJ/cm$^2$) | MPE Multiple Range |
|---|---|---|
| MRE I | 250-400 | 26.26-42.02 × MPE |
| MRE II | 550-650 | 57.77-68.28 × MPE |
| MRE III | 750-850 | 78.78-89.29 × MPE |

As illustrated by the above MPE multiples, the MREs are considerably higher than the MPE. The iris is far less sensitive to excessive radiative exposure, and the consequences of excessive radiative iris exposure are not as severe in any case. In addition, the melanocytes of the fundus (known as the "retinal pigment epithelium" or "RPE") are generally darker and denser than those of the anterior iris, so the absorption coefficients in the fundus are higher. Also, the lens will focus the beam onto the fundus, thereby increasing its energy density at the fundus. Nevertheless, the MREs must be achieved without exceeding the MPEs in case the beam accidentally passes through the pupil (or any other opening in the iris) to the fundus.

In most cases, pulses fired through the pupil and focused onto the fundus will represent a "pulse train." A pulse train occurs where two or more successive pulses fully or partially overlap onto the target plane. This is particularly true in the case of the preferred embodiment, where $\theta_i$ remains at or about 0° throughout the procedure. Even if the beam is moving during the procedure (as assumed), the crystalline lens will focus the pulses onto a single spot on the fundus.

Regardless of the specific iris scan pattern, the beam path will likely cycle between the pupil and the iris. The iris cycles will likely be of sufficient duration to separate the pupil cycles into independent pulse trains. Under these circumstances, the maximum number of pulses in the pulse train (given by N below) will be the diameter of the pre-operative pupil (in mm), divided by the spot separation (in mm). If the operator follows the preferred embodiment below of triple pre-operative dosing with Pilocarpine 2%, the pupil diameter should be ≤1.0 mm. If the spot diameter (at $1/e^2$), for example, were 0.05 mm, and the spot separation were 0.05 mm (i.e., the spots are tangent), then N=1/0.05=20 pulses. Unless otherwise indicated, $1/e^2$ is used to define the beam waist.

Where pulses are members of a pulse train, the MPE calculated above may also be multiplied by an attenuation factor, $C_P$, calculated as follows:

(a) If t≥3 µs, then $C_P$ is given by the following Equation (2):

$$C_P = \left(\frac{dr(t)}{dr(T)}\right) \cdot N^{-0.25} \cdot D^{-0.75} \cdot 0.7^{(1-D)}$$

where
N is the number of pulses in the pulse train;
t is the single pulse width (in seconds);
tp is the period of a single pulse (in seconds);
T is the duration of the pulse train (in seconds), equal to the value N×tp;
D is the duty cycle of the pulse, equal to t/tp;
dr(t) is the dr (in mm) for a pulse of duration t, up to a maximum of dr(t)=3.4 $t^{0.5}$; and
dr(T) is the dr (in mm) for T, up to a maximum of dr(T)=3.4 $T^{0.5}$.

(b) If t<3 µs, then $C_P$ is given by the following Equation (3):

$$C_P = \frac{10}{d_r(T)} \cdot t^{0.75} \cdot D^{-0.75} \cdot N^{-0.25} \cdot \frac{0.7^{(1-D)}}{MPE}$$

where MPE is expressed in $J/cm^2$.

(c) If $C_P$>1.0. then set $C_P$ at 1.0.

Thus, methods based on the above may include the system determining, concurrently or sequentially with the tracking, the laser power to deliver to stromal pigment by at least retrieving a set of laser criteria for delivery of an exposure less than 100 times of a maximum permissible exposure that will cause elimination of at least a portion of the stromal pigment. The elimination of the stromal pigment is preferably performed by initiation of macrophagic digestion of the stromal pigment. However, in some implementations, the elimination may be caused by ablation of the stromal pigment. Typically, ablation is caused by higher laser powers than those used to initiate macrophagic digestion.

Laser criteria may include any settings for the laser system such as energy per pulse, spot size, pulse duration, pulse width, repetition rate, beam profile, beam angle, beam position, etc. accordingly, it is contemplated that there may be multiple sets of such laser criteria that satisfy the restriction on the exposure described above. While the above multiple is one example, it is further contemplated that the exposure may be, for example, less than 50 times the MPE, less than 75 times the MPE, etc.

In some implementations, the difference given above may be due to the divergence angle of the beam (i.e., a defocused beam causes a lower power density at the fundus). Various implementations may include generation of a Gaussian beam that may be converging anterior (in front of) to the iris with at least a portion diverging posterior (behind) the iris. The focal plane (i.e., the location of the beam waist) may therefore be anywhere in this range, such as being within the iris itself, but optionally further in front of the iris. When the present disclosure refers to focusing laser power at the stromal pigment, this means that the laser power may be focused at a specific location, which may include, the anterior or posterior surface of the iris, or at a particular cell layer in the iris or stromal pigment layer therein.

The divergence of the beam and the size and location of the beam waist set the spot size at the target. For example, if the beam waist is at the target, the spot size is the beam waist. However, if the beam waist is in front or behind the target, the spot size will be larger based on the convergence or divergence of the beam. Because a spot size does not have sharp edges, the measurement must be defined by a specific measurement convention. Exemplary conventions comprise FWHM, 1/e, $1/e^2$, D4σ, 10/90 or 20/80 knife-edge, and D86. Unless otherwise indicated herein, spot size shall refer to spot width, as defined by the $1/e^2$ convention. Some methods may include determining a spot size for laser light to be delivered to a stromal pigment of an iris of the eye of the patient. The determination may include retrieving a set of laser criteria that result in delivery of laser light having a spot size of 4-70 microns, inclusive, to the stromal pigment. From the available set of set of laser criteria, a particular laser criterion may be selected to control the laser system to generate a laser having a desired spot size. The laser system may be set to deliver the laser light at the spot size and then to deliver the laser light. In some embodiments, the system may determine that spot size may be between 4-50, 10-60, 20-30, 25-30, 20-60, or 30-60 microns. Such spot sizes may be created utilizing at least one positive lens. To deliver an efficacious fluence at the iris plane, but comply with the MPE at the fundus, the forming of such a high divergence angle will create a short depth of focus ("DOF"), defined herein as the focal range within which 90% to 100% of peak fluence is achieved). The DOF will depend not only on the spot size and associated divergence angle, but also the wavelength of the beam. In general, the longer the wavelength, the longer the DOF, ceteris paribus. Thus, the present disclosure contemplates that the spot size, in combination with the laser power, may be selected to be sufficient to cause a concurrent temperature change (and/or possible acoustic effect) in the iris, thereby causing initiation of macrophagic digestion of the stromal pigment while being safe for the patient. In some implementations, the spot size of the laser system may be set (and largely constant) with the laser power being adjusted as described herein (to effect treatment, but still have the exposure at the fundus be below the MPE).

While the above is provided as one enabling example suitable for determination of beam waist/spot size, such should not be considered limiting as the particulars of the calculation may change depending on an individual treatment plan.

In order to achieve the MRE without exceeding the MPE, a relatively high beam divergence angle may be used. As a result, the radius of the beam at its focal plane ($w_0$) may be relatively small as compared to the radius of the beam waist at the fundus plane ($w(z)$).

Equation (4) gives the ratio (S) of $w(z)^2$ to $w_0^2$:

$$S = \frac{R(\lambda) \cdot H(J/cm^2)}{0.02}$$

where

The 0.02 denominator is the base MPE of 20 mJ/cm² for $\lambda$=700 nm, converted to J/cm²; and $R(\lambda)$ is the Thermal Hazard Weighting Function for the A from Appendix 1.

Using the laser parameters from the Exemplary Embodiment, $R(\lambda)$=2.10. Equation (4) thus gives the following S ranges:

| MRE | MRE Range (mJ/cm²) | S Range |
|---|---|---|
| MRE I | 250-400 | 25.25-42.00 |
| MRE II | 550-650 | 55.75-68.25 |
| MRE III | 750-850 | 78.75-89.25 |

To avoid having to change $w_0$ for each patient/treatment, a preferred embodiment sets $w_0$ at the highest anticipated MRE so that the $w_0$ will meet the MPE for all MREs. In the example above, the highest anticipated MRE is 0.850 J/cm². This gives us an S of 89.25, meaning that in order to prevent the highest MRE from exceeding the MPE, $w(z)^2$ must be at least 89.25 times $w_0^2$.

To find $w_0$ from S, we can use the following Equation (5):

$$w_o = \sqrt{\frac{\lambda \cdot z}{\pi \cdot n \cdot \sqrt{S-1}}}$$

where $\lambda$=0.000532 mm (converted from 532 nm);

z is the distance in mm from $w_0$ to $w(z)$; and n is the refractive index of the medium through which the beam will travel.

Using 20 mm as the average z from the iris plane to the fundus plane and 1.336 as the n of the aqueous and vitreous fluids of the eye, Equation (5) gives $w_0$=0.0164 mm.

The following Equation (6) may be used to find $w(z)$:

$$w(z) = \sqrt{S \cdot w_0^2}$$

Equation (6) gives $w(z)$=0.15519155 mm.

Recall that $w_0$ and $w(z)$ are the radii of the beam at its waist and at the fundus. Therefore, the diameter (as $1/e^2$) of the beam at its waist ($d_0$) is 0.0328 mm, and the diameter (as $1/e^2$) of the beam at the fundus ($d(z)$) is 0.31038 mm.

The DOF of the beam is the total distance (+/−z) from its beam waist. The distance z is given by the following Equation (7):

$$z = \frac{w_0^2 \cdot \pi \cdot n \cdot \sqrt{S-1}}{\lambda}$$

where

S=1/[desired percentage of waist fluence]

$\lambda$=0.000532 mm

The DOF may be defined as that portion of the beam axis where the fluence of the beam is at least 90% of the fluence at the beam waist, i.e., where S=1/0.9. Using this and the other laser parameters from the disclosed example, Equation (7) gives z=0.707312185 mm, and DOF=1.41462437 mm.

This relatively short DOF demands reasonably high-resolution range-finding to identify the location of the initial focal plane and place the beam waist at the desired location in relation to the initial focal plane, as well as reasonably high resolution auto-focusing to maintain the desired location of the beam waist relative to the focal plane. These high-resolution systems are discussed herein. In one implementation, the beam waist may be located within the stromal pigment layer or slightly anterior to the anterior iris surface.

Figure 3:
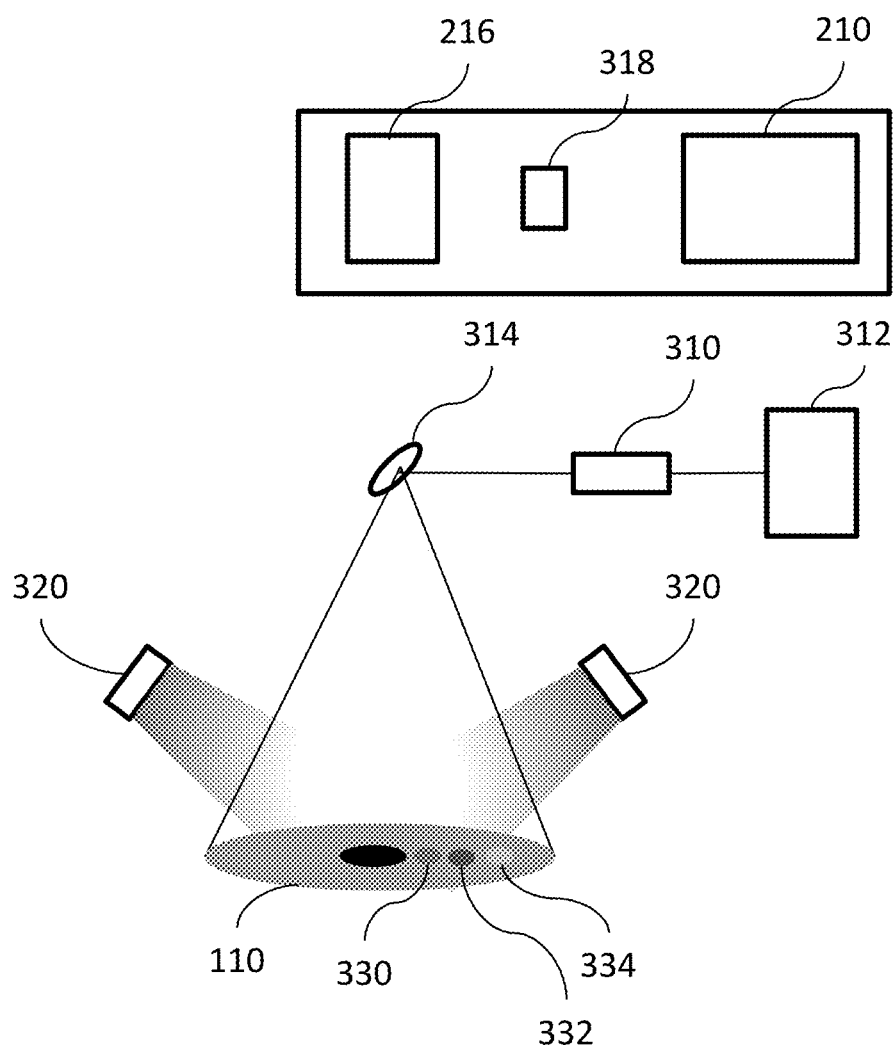
FIG. 3 shows a simplified diagram of a laser system and image sensor for use in mapping the iris in accordance with one or more embodiments.

FIG. 3 shows a simplified diagram of a laser system 210 and image sensor 310 for use in mapping the iris in accordance with one or more embodiments. Determination of the proper laser power may depend on variations in the absorption of the delivered laser power due to inhomogeneities in regions 330, 332, 334 of the stromal pigment layer. Such variations may be caused by, for example, varying density of the stromal pigment, varying sizes of stromal pigment cells, types and compositions of the stromal pigment, etc. As such, regions of the iris where the stromal pigment has a higher absorption coefficient reach a higher temperature (or a target temperature faster) for a given laser power. These differences, if not accounted for, may result in uneven color alteration or possibly even damage to the eye. To address this problem, some implementations of the disclosed methods may include imaging the iris with an image sensor operatively connected to a computer 312 prior to the procedure to generate images of the iris. Examples of image sensors may include a CCD, COMS, or camera used in conjunction with an illumination source 320, wherein the wavelength range of the sensor includes the wavelength of the illumination source. Exemplary wavelengths include near and mid-infrared, visible light, or the specific wavelength of the treatment laser beam. An embodiment might also include software programs capable of creating a digital color model from the captured images and mapping or otherwise analyzing the stromal pigment coefficients for the treatment wavelength based on the model. Exemplary digital color models include RGB (which stands for red-green-blue), HSI (for hue-saturation-intensity), HSL (for hue-saturation-lightness), HSV (for hue-saturation-value), CMY (for cyan-magenta-yellow), and YIQ (luminance-inphase-quadrature).

To facilitate integration of the image sensor with existing laser system, the image sensor may incorporate a dichroic optic 314 (e.g., a dichroic lens, mirror, or prism) to divert incoming light reflected from the iris the reflective or refractive side of the optic and directing it to the image sensor, while allowing outgoing laser light to pass through the optic to the iris surface for treatment. Such implementations have the advantage that the light may be collected on the same optical axis as the laser system. This has the advantage of both simplifying and making more accurate the generation of the mapping relative to the geometry of laser system because it avoids the need to account for an off-axis image sensor.

Based on the images, a mapping of the iris may be generated by the system and may contain regions corresponding to varying absorption coefficients of a treatment wavelength in the stromal pigment of the iris. As shown in FIG. 3, regions 330, 332, 334 are depicted to indicate different absorption coefficients. The mapping may be, for example, 2D (or 3D) data having pixels or voxels of the imaged iris with each pixel or voxel having a corresponding calculated absorption coefficient. The mapping need not be stored at the pixel/voxel level but may also be in terms of larger regions (e.g., combining pixels/voxels that may have similar absorption coefficients (e.g., utilizing a watershed algorithm). In other embodiments, regions may be specified at the subpixel/voxel level by performing 2D (or 3D) interpolation of neighboring pixels/voxels to provide a continuous function of absorption across a pixel/voxel.

As mentioned above, generating the mapping may include calculating absorption coefficients at the wavelength of the laser light in various regions of the iris. The present disclosure contemplates numerous implementations for calculating the absorption coefficients. For example, the image sensor (or data obtained with such) may measure the absorption or reflectivity of predetermined wavelengths within the image of the iris to determine the absorption coefficients. The fluence needed to increase the temperature in the target stromal pigment and thereby initiate the biological reaction necessary to remove the target pigment is a direct function of the absorption of the energy of the laser light in the pigment. Thus, by determining the absorption coefficient of the stromal pigment in a particular region for the given wavelength, the system can accurately determine and deliver the laser power needed for pigment removal.

The system may include various apparatuses for determining the absorption coefficients, such as those used with hyperspectral imaging ("HSI"); scanning electron microscopy ("SEM") images with color modeling (e.g., RBG, HSI, HSL, HSV, CMY, and YIQ) using filters appropriate for the laser wavelength.

To map the pigment density, various kinds of light may be used by the system, for example, infrared or visible. In some implementations, the saturation channel of an iris image may provide a very good estimate of stromal pigment density. In other embodiments, the system may use blue or green channels of the image. In yet other embodiments, the system may use monochrome infrared for an approximation of stromal pigment.

Specifically, in some embodiments, the reflectivity of the image is based on an inverse of the saturation in the image. The system may determine reflectivity, saturation, etc., on a pixel by pixel basis or over wider regions of the image. For example, based on analyzing intensities of received light at the imaging sensor, the system may break up the iris into regions of similar intensities (e.g., within 1%, 5%, 10%, etc.). The system may determine the average reflectivity and/or saturation of these regions for determining the absorption coefficient for all points of delivery of light in that region.

Several optional features are disclosed to aid in obtaining more accurate measurements for determining absorption coefficients. First, the illumination source may have the same (or approximately the same—e.g., within 5% or 10%) of the wavelength delivered by the laser system. For example, if the planned treatment incorporates a 1064 nm laser, then the illumination source may provide infrared light covering that wavelength. Similarly, if the laser wavelength is to be 532 nm (green), then the illumination source may provide green light. Also, in certain implementations, this imaging may further include filtering the reflected light received from the stromal pigment at the image sensor through a bandpass filter configured to pass a wavelength corresponding to the laser light and/or illumination source. In yet other implementations, the system may include a similar bandpass filter at the illumination source, for example, if such sources are more broad-spectrum than desired.

The laser system may also include a power modulator 318 to vary the laser power based on the determined mapping. Exemplary optical power modulators may include: acousto-optic modulators; electro-optic intensity modulators; electro-absorption modulators; semiconductor optical amplifiers; and liquid crystal modulators. A structural embodiment of an exemplary acousto-optic modulator may include a transducer that generates a sound wave that partially diffracts the laser beam. A structural embodiment of an exemplary electro-optic intensity modulator may include a Pockels cell between two polarizers. The Pockels cell modulates the phase of the beam, and the polarizers transform the phase modulation into an intensity modulation. The Pockels cell may have a single crystal or two or more crystals to reduce its power requirements. The polarizers may be replaced by an interferometer, as in the case of a Mach-Zehnder modulator. A structural embodiment of an exemplary electroabsorption modulator may include one or more semiconductor devices operating on the Franz-Keldysh effect. Such modulators may operate on light in a waveguide and may be coupled to optical fibers or placed on a chip together with other components, such as a laser diode to form a telecom transmitter. An exemplary semiconductor optical amplifier used as an intensity modulator includes a semiconductor optical amplifier, with or without drive current. Without drive current, the amplifier provides some degree of attenuation as negative gain. When supplied with pump current, attenuation is achieved as positive gain. An exemplary liquid crystal modulator applies a voltage to a liquid crystal material to modulate light polarization and obtain intensity modulation by adding a polarizer.

Figure 4:
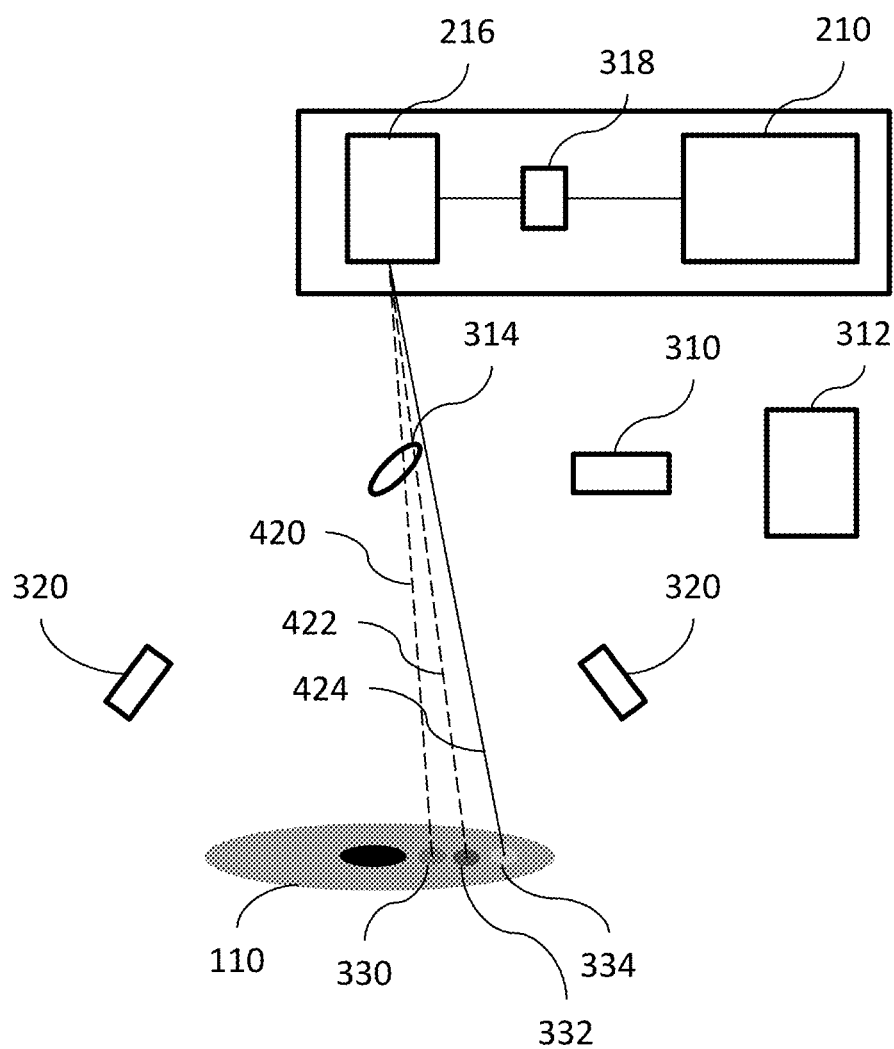
FIG. 4 shows the system of FIG. 3 delivering variable laser power to regions of the iris in accordance with one or more embodiments.

FIG. 4 shows the system of FIG. 3 delivering variable laser power to regions of the iris in accordance with one or more embodiments. With the mapping derived as noted herein, the power modulator may control delivery of laser power that accounts for the regions having different absorption coefficients. As the laser light scans the target areas of the iris, when a region is reached that is a different absorption coefficient, the system may control the power modulator to adjust the laser power accordingly. For example, the system may set the laser power based on the mapping such that regions of higher absorption coefficients receive a lower laser power than regions of lower absorption coefficients. This is depicted by exemplary laser beams 420, 422, and 424 which correspond to the regions 330, 332, and 334. The system may modulate the laser power delivered with such beams utilizing the power modulator described above.

The system may also be configured for blanking the beam wherever there is little or no stromal pigment. Beam blanking can be accomplished in a number of ways, including deactivating the laser, deflecting the beam into a beam dump using an optic such as a prism or mirror, or reducing the radiative power to a subclinical level using the energy modulator disclosed elsewhere in this Application. Deactivating the laser may, in some cases not be utilized due to time delays and other potential complications upon reactivation.

In one embodiment, anterior iris regions are selected or deselected for blanking automatically by illuminating the anterior iris, using a CCD or other camera to capture an image of the anterior iris surface, transmitting the image to a computer with an image analysis software program (such as Celleste Image Analysis Software, Thermo Fisher Scientific Inc., Waltham, Mass., USA), identifying the pigmented regions, generating a lookup table comprising the coordinate ranges of the pigmented regions, and coordinating with the beam guidance software and energy disruption or modulation software to blank the treatment beam everywhere outside of the pigmented regions.

In an alternate embodiment, anterior iris regions may be selected or deselected for blanking manually by automatically by the system illuminating the anterior iris, capturing a still or moving image a CCD or other camera, displaying the image on the user interface touch screen, inviting the operator to outline the regions he or she wishes to blank or irradiate, and inviting to operator to elect (e.g., via icons on a GUI displayed on the same screen) whether the outlined areas are to be treated or blanked. The display computer and software may display the operator-drawn outlines on the display, generate a lookup table comprising the coordinate ranges of the outlines, and coordinate with the beam guidance software and energy disruption or modulation software to blank the treatment beam everywhere inside or outside (as selected) of the outlined regions.

One of the advantages of these selective beam blanking implementations is that without it, re-treating the anterior iris surface after the pigment has been removed might result in the elimination of additional stromal pigment from within the iris stroma, which, as discussed herein, will likely increase color saturation, which might be contrary to the patient's preferences.

Some implementations of the disclosed methods may include utilizing a rangefinder as part of the optical tracking system to provide accurate distances to the target location in the eye. For example, the rangefinder may determine a distance between the iris and a reference component of the optical tracking system. Examples of reference components may include the last optical component in the laser system (e.g., a window or lens closest to the patient), a mirror or galvos, or any other component or location in the laser system with a known location to provide a point of reference for the rangefinding.

Based on the determined distance, the system may control shift the focal point of the laser beam to remain substantially in focus between an anterior surface and posterior surface of the iris, at the stromal pigment targeted for removal, or at any of the disclosed possible focusing planes. Examples of rangefinders may include, for example, triangulation lasers, time of flight detectors, phase shift detectors, ultrasonic detectors, frequency modulation detectors, interferometers, a camera, or a light sensor.

Triangulation may utilize lasers for distance measurements. Structural embodiments of exemplary triangulation methods may include three elements: an imaging device, an illumination source, and either an additional imaging device or an additional illumination source. Illumination source(s) may include image projectors that project light images onto the iris, sclera, or other patient field. Exemplary light images might include circles and lines. In one embodiment, the laser beam may illuminate a point on the surface of the target (e.g., the iris, the sclera, or some other point on the patient's face). Diffuse or specular reflections from the illuminated point may be monitored with a position-sensitive detector, which may be placed a given distance from the laser source such that the laser source, the target point, and the detector form a triangle. Assuming the beam incidence angle to the target is 0°, the position-sensitive detector identifies the incidence angle of the detector to the target, and the distance between the laser source and the detector is known, the distance from the laser source to the target may be determined with the appropriate trigonometric function.

Time-of-flight or pulse measurements may measure the time of flight of a radiation pulse from the measurement device to the target and back again. Exemplary forms of radiation include light (e.g., near-infrared laser) and ultrasound. An exemplary time-of-flight apparatus includes a radiation source, a radiation sensor, and a timer. Time of flight may be measured based upon timed pulses or the phase shift of an amplitude modulated wave. In the case of timed pulses, the speed of the radiation is already known, so the timer measures the turnaround time of each pulse to determine the distance, where distance=(speed of radiation×time of flight)/2.

The phase shift method may utilize an intensity-modulated laser beam. The phase shift of intensity modulation may be related to the time of flight. Compared with interferometric techniques, its accuracy is lower, but it allows unambiguous measurements over larger distances and is more suitable for targets with diffuse reflection. For small distances, ultrasonic time-of-flight methods may be used, and the device may contain an aiming laser for establishing the direction of the ultrasonic sensor, but not for the distance measurement itself.

Frequency modulation methods may include frequency-modulated laser beams, for example with a repetitive linear frequency ramp. The distance to be measured may be translated into a frequency offset, which may be measured via a beat note of the transmitted and received beam.

Interferometers may be implemented for distance measurements with an accuracy which is far better than the wavelength of the light used.

Various systems for rangefinding may provide very accurate measurements, for example, determining distances with the resolution of at least 10-20 μm. Such systems may include, for example, a time-domain optical coherence tomography system or a spectral domain optical coherence tomography system.

Utilizing the disclosed rangefinding, some methods may utilize the same structure to include autofocusing the laser system in response to changes in the determined distance and corresponding shifts in the focal point of the beam. Computer systems in communication with the laser system may automatically autofocus the laser system and measure a distance to the stromal pigment of the iris at periodic intervals (e.g., at approximately 1 kHz, 10 kHz, 100 kHz, etc.).

Exemplary methods for lens focusing include manually or electronically (a) shifting the position of one or more focal lenses (e.g., a lens mounted on a motor stage to shift along the beam access), (b) shifting the position of one or more focal mirrors (e.g., by adding a third mirror to a galvos beam steering system), (c) changing the shape of one or more focal lenses or mirrors, (d) deflecting or refracting a beam by means of an acousto-optical or electro-optical devices, or (e) using electrostatic or electromagnetic lenses or mirrors to shift the focal position of the beam.

Movement of the patient's head and eyes along the z axis can frustrate accurate range-finding and autofocusing. By positioning the patient such that the head is supported and the neck muscles are permitted to release, z head position changes may be minimized.

Topographical variations in the anterior iris surface may also frustrate accurate range-finding and autofocusing. These variations result primarily from three elements: iris tilt, iris folds, and iris crypts. Iris tilt is a naturally occurring phenomenon. As a result, the iris plane will rarely reside perpendicular to the beam axis. The iris plane tilts about both its the horizontal and vertical axes, and can tilt as much as 5°, which results in z variations of up to 700 μm from one edge of the iris to the other (assuming a roughly 11 mm horizontal iris diameter). An iris tilt system may be utilized to significantly reduce or eliminate this iris surface variation.

Iris folds are also a naturally occurring phenomenon. As the iris dilates, it folds like a drape, concentric to and away from the pupil. These folds can create significant z variations in the iris topography. To significantly reduce or eliminate iris folds, some methods may include introduction of a topical miotic solution, such as Pilocarpine ophthalmic solution. In one embodiment, patents may be dosed with 1 drop of 2% Pilocarpine ophthalmic solution 15, 10, and 5 minutes prior to the procedure to achieve high miosis, resistant to the potentially dilative effect of lasing the iris anterior to the iris dilator muscles during the procedure. Each patient may also be given 500 mg of acetaminophen (orally) 30 minutes prior to the procedure as a prophylaxis against headaches from ciliary body tension.

Iris crypts are another common phenomenon. They are created by spaces between the iris stromal fibers. In brown eyes, these crypts are typically filled with pigment and can therefore be ignored for purposes of the initial treatment sessions. Once the stromal pigment has been substantially eliminated outside of the crypts, stromal pigment might remain in the depths of the iris crypts. Pigment spots occur naturally in light eyes, so this remaining crypt pigment should not look unnatural and should barely be noticeable.

If remaining pigment spots bother the patient, the system can remove or reduce the remaining crypt pigment by based on a current stage of delivery and delivering the laser power based on the setting. A treatment session may include any number of stages of delivery, though typically a treatment session includes only one stage of delivery as days or weeks may be needed for removal of the denatured stromal pigment.

In some implementations, the system may deliver laser power over a number of steps to allow finer control of pigment denaturation. This may be a safety feature of the system to ensure that the lowest power is applied to the cells with the highest absorption coefficient to avoid ablation, that the highest power is applied to the cells with the lowest absorption coefficient to achieve efficacy, and that the intermediate powers are applied to the cells with the intermediate absorption coefficients to avoid ablation and achieve efficacy.

For example, as illustrated below, in one exemplary embodiment based on the above-described multiples of MPE, an arbitrary number of sub-ranges can be established and laser power may be delivered within those subregions. In the table below, the "Total Range" is reproduced from above. For each of the eye colors, an example five sub-ranges are shown, but the system may deliver any number of sub-ranges (e.g., 2, 3, 7, 10, etc.) of laser power. Another optional feature reflected in the below example is that the sub-ranges are chosen to overlap with the adjacent sub-range. In the example below, the overlap is 20%, however, this can vary in other implementations for example, 5%, 10%, 30%, etc.

| Color | Total Range (x MPE) | Subrange I (x MPE) | Subrange II (x MPE) | Subrange III (x MPE) | Subrange IV (x MPE) | Subrange V (x MPE) |
|---|---|---|---|---|---|---|
| Dark Brown | 25.4-42.6 | 25.4-26.6 | 29.4-30.6 | 33.4-34.6 | 37.4-38.6 | 38.4-42.6 |
| Medium Brown | 57.5-71 | 57.5-61 | 60-63.5 | 62.5-66 | 65-68.5 | 67-71 |
| Tan | 78.5-92 | 78.5-82 | 81-83.5 | 62.5-87 | 86-90.5 | 88-92 | slightly shifting the beam waist posteriorly into the stroma and rescanning the iris using this shifted waist position. This shifted waist setting may also be an option displayed for selection by the operator on the touch screen interface. The distance of the shift of the beam waist may be equal to about 80% of the beam DOF to ensure delivery of high fluence within the pigmented crypts. If the crypt pigment remains 3-4 weeks after treatment with this posterior waist shift, this waist shift procedure may be repeated, posteriorly shifting the beam waist each time by another 80% of the DOF, until the crypt pigment is eliminated sufficiently eliminated.

The color alteration procedure described herein may be divided into multiple stages of treatment to remove different amounts or types of stromal pigment at different times. Stromal pigment, as previously discussed, may have varying physical properties that affect its responses to delivered laser power. Some stromal pigment may require a higher laser power to raise its temperature such that it may be removed via macrophagic digestion. Thus, after a first treatment at a lower power, there may be some stromal pigment that needs to be removed and require a higher laser power to do so. In this way, some methods of treatment may include determining, as part of the color alteration procedure, stages of delivery of laser power to the iris such that successive stages cause removal of less pigment but are delivered at a higher laser power. Thus, a given treatment session may include setting the laser system to the required laser power further Thus, in one implementation, the system may be configured to provide multistage delivery where there are at least three stages. In this example (for dark brown eyes), a first stage of the three stages may deliver approximately 26 times MPE to the stromal pigment, a second stage may deliver approximately 30 times the MPE to the stromal pigment, and a third stage may deliver approximately 34 times the MPE to the stromal pigment.

Some methods of the present disclosure may further include determining the proper amount of laser power to deliver based on a patient's immune response. Because macrophagic digestion is one method of removing stromal pigment, and activation of macrophages is an immune response, the removal of the stromal pigment is proportional to the patient's immune response. Accordingly, some methods may include prescreening patients to determine the efficiency or aggressiveness of his or her macrophagic response to laser disruption of stromal melanocytes, thereby further informing the MPE and MRE. The macrophagic response data could be entered into the system computer for calculation of any adjustments to the baseline fluence settings.

Based on the immune response, the system may tailor the time interval between treatment stages to a particular person. This may include comparing the immune response level to a range of immune responses associated with a time interval between two of the stages. For example, two stages could be separated by 3-4 weeks based on a typical immune response (e.g., a 5 on a 1-10 scale, 10 being the highest immune response). The treatment procedure could have treatment intervals of 2-3 weeks for patients with an immune response rated between 8 and 10, and 5-6 weeks for patients with an immune response rated between 1 and 3. The method may then include, for example, reducing the time interval based on the comparing showing that the immune response level is higher than the range. The system may make a similar adjustment to the interval based on knowledge of a patient's inflammatory response. Examples of possible inflammatory response tests may include skin tests, where a patient is exposed to a substance expected to cause an allergic reaction. The data representative of the inflammatory response level quantifies the result of the skin test and may be used as described above. Similarly, in some embodiments, quantification of the immune response may be used to reduce or increase the laser power in any given treatment session and/or reduce or expand the time between treatments. For example, if the immune response shows that removal of pigment will occur 50% faster than a given baseline (e.g., for a typical immune response) then the time between sessions may be reduced by 50%.

In addition, inflammation is also an immune response to free melanin in the anterior chamber of the eye. Accordingly, prescreening patients to determine the aggressiveness of their immune responses to free melanin may be utilized by the system for adjustment or determination of the MPE and MRE, and the inflammatory response data may be utilized by the system for calculation of any adjustments to the baseline fluence settings. For macrophagic response to thermal disruption of stromal pigment, testing for the prevalence of cleaved caspase-1 p20 (a marker for inflammasome activation) and pro-inflammatory cytokines IL-1β and IL-6, both at baseline and perhaps in response to some perturbation to test reactivity may be used by the system. The system, in determining an inflammatory response to free melanin in the AC, may test or use results from tests for the prevalence of CD4+ T cells, angiogenin (AG), and pro-inflammatory cytokines (such as IL-1α, IL-1β, TNF-α, MMP-9. IL-2, IL-17), again, both at baseline and optionally in response to treatment.

Figure 5:
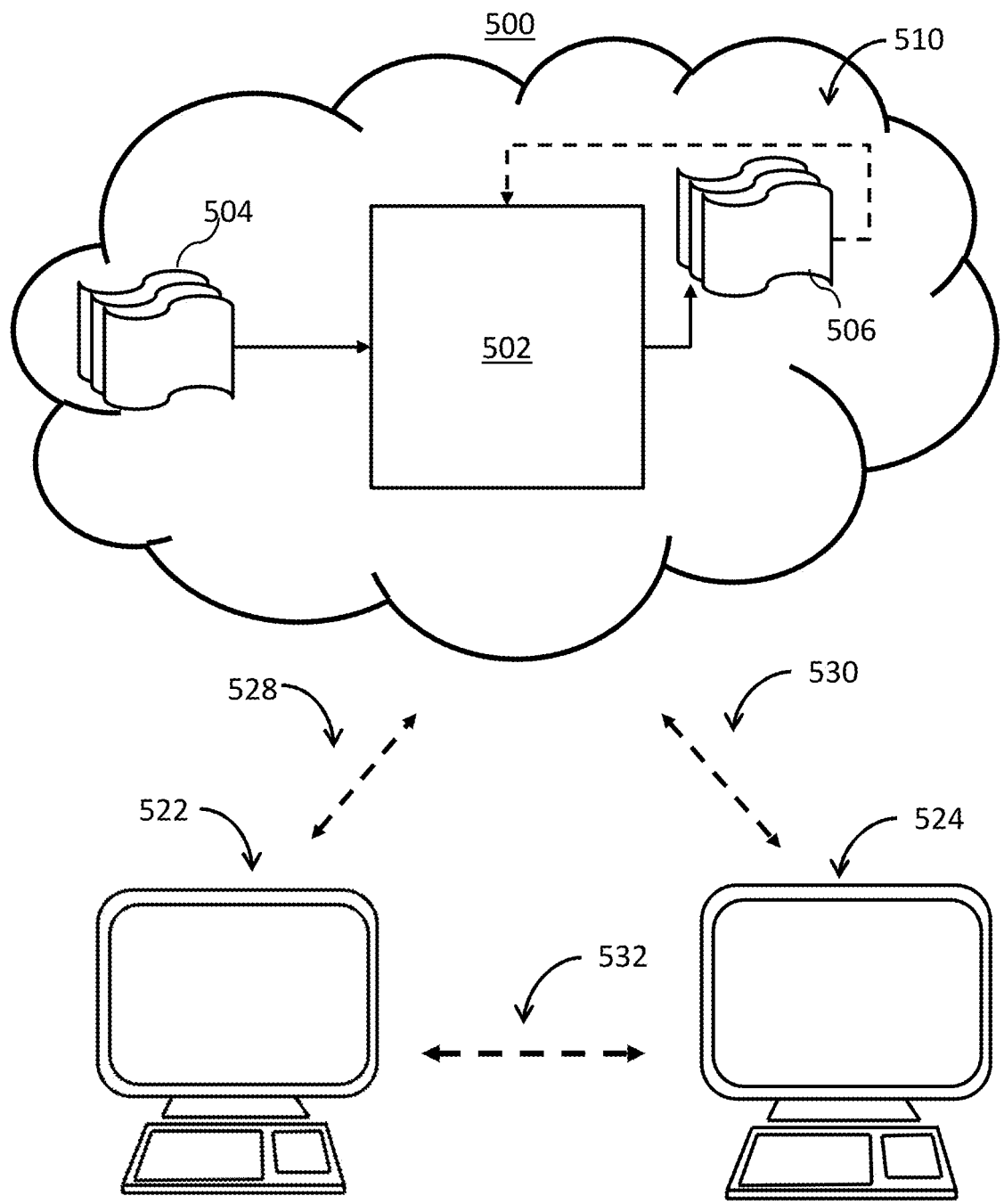
FIG. 5 shows an illustrative system for performing an eye color changing procedure in accordance with one or more embodiments.

FIG. 5 shows an illustrative system for performing an eye color changing procedure in accordance with one or more embodiments. For example, system 500 may represent the components used for performing an eye color changing procedure. For example, system 500 may power a local device to perform an eye color changing procedure where the required determination (e.g., pattern to follow, laser power to deliver, identification of patient, etc.) are determined remotely and/or in the cloud. As shown in FIG. 5, system 500 may include user terminal 522 and user terminal 524. While shown as personal computers, in FIG. 5, it should be noted that user terminal 522 and user terminal 224 may be any computing device, including, but not limited to, a laptop computer, a tablet computer, a hand-held computer, other computer equipment (e.g., a server), including "smart," wireless, wearable, and/or mobile devices. FIG. 5 also includes cloud components 510. Cloud components 510 may alternatively be any computing device as described above and may include any type of mobile terminal, fixed terminal, or other device. For example, cloud components 510 may be implemented as a cloud computing system and may feature one or more component devices. It should also be noted that system 500 is not limited to three devices. Users may, for instance, utilize one or more other devices to interact with one another, one or more servers, or other components of system 500. It should be noted that, while one or more operations are described herein as being performed by particular components of system 500, those operations may, in some embodiments, be performed by other components of system 500. As an example, while one or more operations are described herein as being performed by components of user terminal 522, those operations may, in some embodiments, be performed by components of cloud components 510. In some embodiments, the various computers and systems described herein may include one or more computing devices that are programmed to perform the described functions. Additionally, or alternatively, multiple users may interact with system 500 and/or one or more components of system 500. For example, in one embodiment, a first user and a second user (e.g., a technician and a physician) may interact with system 500 using two different components.

With respect to the components of user terminal 522, user terminal 524, and cloud components 510, each of these devices may receive content and data via input/output (hereinafter "I/O") paths. Each of these devices may also include processors and/or control circuitry to send and receive commands, requests, and other suitable data using the I/O paths. The control circuitry may comprise any suitable processing circuitry. Each of these devices may also include a user input interface and/or user output interface (e.g., a display) for use in receiving and displaying data. For example, as shown in FIG. 5, both user terminal 522 and user terminal 524 include a display upon which to display data (e.g., information related to an eye color changing procedure).

Additionally, as user terminal 522 and user terminal 524 are shown as touchscreen smartphones, these displays also act as user input interfaces. It should be noted that in some embodiments, the devices may have neither user input interface nor displays and may instead receive and display content using another device (e.g., a dedicated display device such as a computer screen and/or a dedicated input device such as a remote control, mouse, voice input, etc.). Additionally, the devices in system 500 may run an application (or another suitable program). The application may cause the processors and/or control circuitry to perform operations related to an eye color changing procedure.

Each of these devices may also include electronic storages. The electronic storages may include non-transitory storage media that electronically stores information. The electronic storage media of the electronic storages may include one or both of (i) system storage that is provided integrally (e.g., substantially non-removable) with servers or client devices or (ii) removable storage that is removably connectable to the servers or client devices via, for example, a port (e.g., a USB port, a firewire port, etc.) or a drive (e.g., a disk drive, etc.). The electronic storages may include one or more of optically readable storage media (e.g., optical disks, etc.), magnetically readable storage media (e.g., magnetic tape, magnetic hard drive, floppy drive, etc.), electrical charge-based storage media (e.g., EEPROM, RAM, etc.), solid-state storage media (e.g., flash drive, etc.), and/or other electronically readable storage media. The electronic storages may include one or more virtual storage resources (e.g., cloud storage, a virtual private network, and/or other virtual storage resources). The electronic storages may store software algorithms, information determined by the processors, information obtained from servers, information obtained from client devices, or other information that enables the functionality as described herein.

FIG. 5 also includes communication paths 528, 530, and 532. Communication paths 528, 530, and 532 may include the Internet, a mobile phone network, a mobile voice or data network (e.g., a 5G or LTE network), a cable network, a public switched telephone network, or other types of communications network or combinations of communications networks. Communication paths 528, 530, and 532 may separately or together include one or more communications paths, such as a satellite path, a fiber-optic path, a cable path, a path that supports Internet communications (e.g., IPTV), free-space connections (e.g., for broadcast or other wireless signals), or any other suitable wired or wireless communications path or combination of such paths. The computing devices may include additional communication paths linking a plurality of hardware, software, and/or firmware components operating together. For example, the computing devices may be implemented by a cloud of computing platforms operating together as the computing devices.

Cloud components 510 may be a database configured to store user data for a user. For example, the database may include user data that the system has collected about the user through prior operations and/or procedures. Alternatively, or additionally, the system may act as a clearing house for multiple sources of information about the user. Cloud components 510 may also include control circuitry configured to perform the various operations needed to perform an eye color changing procedure.

Cloud components 510 include machine learning model 502. Machine learning model 502 may take inputs 504 and provide outputs 506. The inputs may include multiple data sets such as a training data set and a test data set. Each of the plurality of data sets (e.g., inputs 504) may include data subsets related to user data, an eye color changing procedure, patient progress, and/or results. In some embodiments, outputs 506 may be fed back to machine learning model 502 as input to train machine learning model 502 (e.g., alone or in conjunction with user indications of the accuracy of outputs 506, labels associated with the inputs, or with other reference feedback information). In another embodiment, machine learning model 502 may update its configurations (e.g., weights, biases, or other parameters) based on the assessment of its prediction (e.g., outputs 506) and reference feedback information (e.g., indication of accuracy, results of procedure, reference labels, and/or other information). In another embodiment, where machine learning model 502 is a neural network, connection weights may be adjusted to reconcile differences between the neural network's prediction and the reference feedback. In a further use case, one or more neurons (or nodes) of the neural network may require that their respective errors are sent backward through the neural network to facilitate the update process (e.g., back-propagation of error). Updates to the connection weights may, for example, be reflective of the magnitude of error propagated backward after a forward pass has been completed. In this way, for example, the machine learning model 502 may be trained to generate better predictions (e.g., predictions related to an appropriate pattern to follow, laser power, level of eye color change, number of procedures, length of procedures, etc.

In some embodiments, machine learning model 502 may include an artificial neural network. In such embodiments, machine learning model 502 may include an input layer and one or more hidden layers. Each neural unit of machine learning model 502 may be connected with many other neural units of machine learning model 502. Such connections may be enforcing or inhibitory in their effect on the activation state of connected neural units. In some embodiments, each individual neural unit may have a summation function which combines the values of all of its inputs together. In some embodiments, each connection (or the neural unit itself) may have a threshold function such that the signal must surpass before it propagates to other neural units. Machine learning model 502 may be self-learning and trained, rather than explicitly programmed, and may perform significantly better in certain areas of problem solving, as compared to traditional computer programs. During training, an output layer of machine learning model 502 may correspond to a classification of machine learning model 502 and an input known to correspond to that classification may be input into an input layer of machine learning model 502 during training. During testing, an input without a known classification may be input into the input layer, and a determined classification may be output.

In some embodiments, machine learning model 502 may include multiple layers (e.g., where a signal path traverses from front layers to back layers). In some embodiments, back propagation techniques may be utilized by machine learning model 502 where forward stimulation is used to reset weights on the "front" neural units. In some embodiments, stimulation and inhibition for machine learning model 502 may be more free-flowing, with connections interacting in a more chaotic and complex fashion. During testing, an output layer of machine learning model 502 may indicate whether or not a given input corresponds to a classification of machine learning model 502 (e.g., an eye color change requested, a pattern to follow, a laser power to deliver, etc.).

Figure 6:
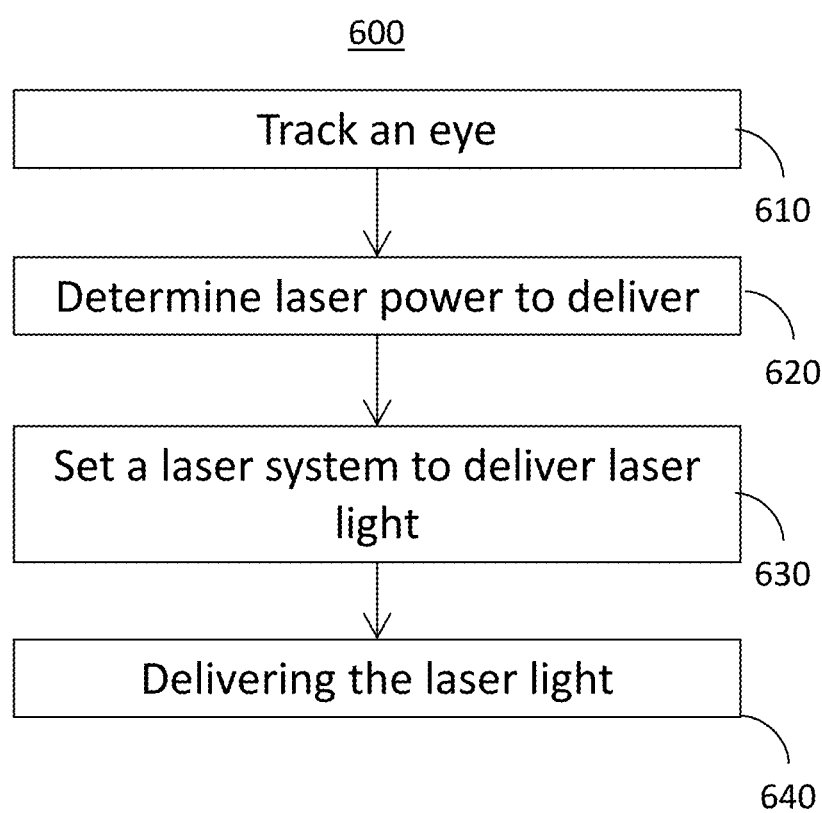
FIG. 6 shows steps for determining laser power for a laser system in accordance with one or more embodiments.

FIG. 6 shows steps for determining laser power for a laser system. For example, process 600 may represent the steps taken by one or more devices as shown in FIGS. 1-5 when performing an eye color changing procedure. For example, process 600 may represent the determinations made by system 500 to power a laser system (e.g., as discussed in FIGS. 2-4).

At step 610, process 600 (e.g., via one or more components of FIGS. 1-5) may track an eye. For example, the system (e.g., via control circuitry) may track, with an optical tracking system, the eye of the patient during the color alteration procedure. In some embodiments, the system may image the iris with an image sensor prior to the procedure to generate images of the iris. Based on the images, the system may generate a mapping of the iris, the mapping with regions corresponding to varying absorption coefficients of a treatment wavelength of the stromal pigment of the iris. Based on the mapping, the system may set the laser system to deliver laser light at a first laser power to a location in the eye of the patient, wherein the first laser power is sufficient to cause elimination of at least a portion of stromal pigment in the iris.

In some embodiments, the optical tracking system includes a rangefinder and the process 600 may include the rangefinder determining a distance between the iris and a reference component of the optical tracking system. The system may determine the with a resolution of at least 10 microns. The rangefinder may be a time-domain optical coherence tomography system or a spectral domain optical coherence tomography system. The reference component may be the last lens in the optical tracking system. In some embodiments, the system may autofocus the laser system in response to the distance. The autofocusing may include measuring a distance to the stromal pigment of the iris at periodic intervals and controlling, by the system and based on the distance, the laser system to remain substantially in focus between an anterior surface and posterior surface of the iris. In some embodiments, the rangefinder may include one or more of: triangulation lasers, time of flight detectors, phase shift detectors, ultrasonic detectors, frequency modulation detectors, interferometers, a camera, or a light sensor.

At step 620, process 600 (e.g., via one or more components of FIGS. 1-5) may determine laser power to deliver. For example, the system (e.g., via control circuitry) may determine a laser power to deliver to stromal pigment in the iris by retrieving a set of laser criteria. The laser criteria may specify delivery of an exposure less 100 times a maximum permissible exposure that will cause elimination of at least a portion of the stromal pigment without injury to the iris or fundus. The system may retrieve the laser power from a database that stores information specific to a user, determine optimal laser power (e.g., via machine learning model 502 (FIG. 5), and/or other information related to an eye color changing procedure).

In some embodiments, the laser power may be at least 20 times the MPE such that a reduction of the laser power below the 20 times the MPE does not cause loosening of the stromal pigment and the resultant change in eye color.

In some embodiments, the elimination may be caused by, and the system may monitor for, initiation of macrophagic digestion of the stromal pigment and/or ablation of the stromal pigment. In some embodiments, the laser power may be sufficient to cause a concurrent temperature change in the iris causing macrophages in the patient to remove at least a portion of the stromal pigment.

At step 630, process 600 (e.g., via one or more components of FIGS. 1-5) may set a laser system to deliver laser light. For example, the system (e.g., via control circuitry) may set the laser system to deliver laser light at a laser power less than specified by the set of laser criteria. The system may set the laser power based on data retrieved from the database in step 620. Additionally, or alternatively, the system may determine a pattern or route to follow during the procedure. For example, the system may determine to deliver the laser light in a scanning pattern (e.g., a spiral pattern surrounding the pupil, which limits the sharp angles and abrupt changes in direction that may increase the length of the procedure, increase a potential for irritation/damage to the eye, and/or risk uneven application) to the entire iris.

At step 640, process 600 (e.g., via one or more components of FIGS. 1-5) may deliver the laser light. For example, the system (e.g., via control circuitry) may deliver the laser light with the laser system (e.g., system 200 (FIG. 2)). For example, the system may deliver the laser light to the anterior border layer or to the deeper stroma layer of the iris (e.g., iris stroma 112 (FIG. 1)). In some embodiments, process 600 may be repeated several times to repeatedly raise and lower the temperature of the stromal pigment. This raising and lowering of the temperature causes the stromal melanocytes to recruit macrophages (part of the body's natural immune response) to the stromal layer. These macrophages then digest and remove through the iris vasculature a portion of the stromal pigment responsible for giving the eye its brown color. The system may repeat process 600 to provide varying degrees of color change to make the eye appear a deeper blue/green. In some embodiments, the system may monitor, with a temperature sensor, the temperature of at least a portion of the stromal pigment and control the laser system to deliver the laser power such that the delivery does not raise the temperature of the stromal pigment to more than 125° C. degrees, as monitored with the temperature sensor. In some embodiments, a target temperature of 120° C. may be set by the system. Thus, in some embodiments, the temperature sensor may be configured to monitor for delivery of laser power that raises the temperature to 115-125° C.

In some implementations, process 600 may include the system determining, as part of the color alteration procedure, stages of delivery of laser power to the iris such that successive stages cause removal of less pigment, but are delivered at a higher laser power. The system may set the laser system to the laser power further based on a current stage of delivery and then deliver the laser power based on the setting. There may be three stages and, in some embodiments, a first stage of the three stages delivers approximately 26 times the MPE to the stromal pigment, a second stage of the three stages delivers approximately 30 times the MPE to the stromal pigment, a third stage of the three stages delivers approximately 34 times the MPE to the stromal pigment. The system may determine an immune response level of a patient based on accessing, by a control computer in communication with the laser system, a medical record of the patient containing data representative of the immune response level. The system may compare the immune response level to a range of immune responses associated with a time interval between two of the stages and reduce the time interval based on the comparing showing that the immune response level is higher than the range. The data may be representative of the immune response level quantifies the result of a pro-inflammatory cytokines test performed on the patient.

Figure 7:
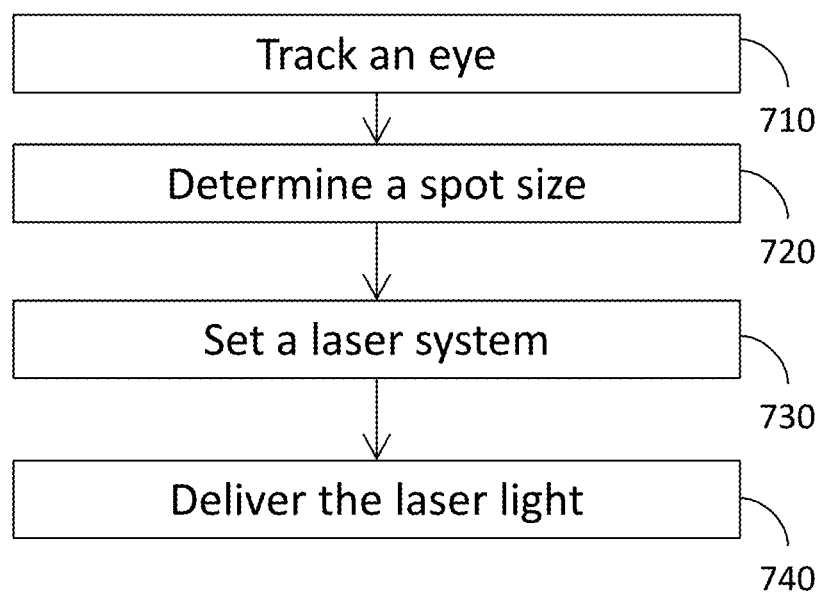
FIG. 7 shows steps for determining spot size for a laser system in accordance with one or more embodiments.

FIG. 7 shows steps for determining spot size for a laser system. For example, process 700 (e.g., via one or more components of FIGS. 1-5) may represent the steps taken by one or more devices as shown in FIGS. 1-5 when performing an eye color changing procedure. For example, process 700 may represent the determinations made by system 500 to power a laser system (e.g., as discussed in FIGS. 2-4). In some embodiments, the elimination may be caused by, and the system may monitor for, initiation of macrophagic digestion of the stromal pigment and/or ablation of the stromal pigment. In some embodiments, the laser power may be sufficient to cause a concurrent temperature change in the iris causing macrophages in the patient to remove at least a portion of the stromal pigment. In some embodiments, the system may image the iris with an image sensor prior to the procedure to generate images of the iris. Based on the images, the system may generate a mapping of the iris, the mapping with regions corresponding to varying absorption coefficients of a treatment wavelength of the stromal pigment of the iris. Based on the mapping, the system may set the laser system to deliver laser light at a first laser power to a location in the eye of the patient, wherein the first laser power is sufficient to cause elimination of at least a portion of stromal pigment in the iris.

At step 710, process 700 (e.g., via one or more components of FIGS. 1-5) track an eye. For example, the system may (e.g., via control circuitry) track, with an optical tracking system, the eye during the color alteration procedure. In some embodiments, the optical tracking system includes a rangefinder and the process 600 may include the rangefinder determining a distance between the iris and a reference component of the optical tracking system. The system may determine the distance with a resolution of at least 10 microns. The rangefinder may be a time-domain optical coherence tomography system or a spectral domain optical coherence tomography system. The reference component may be the last lens in the optical tracking system. In some embodiments, the system may autofocus the laser system in response to the distance. The autofocusing may include measuring a distance to the stromal pigment of the iris at periodic intervals and controlling, by the system and based on the distance, the laser system to remain substantially in focus between an anterior surface and posterior surface of the iris. In some embodiments, the rangefinder may include one or more of: triangulation lasers, time of flight detectors, phase shift detectors, ultrasonic detectors, frequency modulation detectors, interferometers, a camera, or a light sensor.

At step 720, process 700 (e.g., via one or more components of FIGS. 1-5) determine a spot size. For example, the system may (e.g., via control circuitry) determine a spot size for laser light to be delivered to the stromal pigment. This implementation may include retrieving a set of laser criteria that result in delivery of laser light having a spot size of 10-40 microns to the iris. In some embodiments, the spot size may be between 25-30 μm.

At step 730, process 700 (e.g., via one or more components of FIGS. 1-5) set a laser system. For example, the system may (e.g., via control circuitry) seta laser system to deliver the laser light at the spot size.

In some embodiments, the system may determine, with a temperature sensor, a temperature of at least a portion of the iris that contains stromal pigment, where the temperature sensor may be non-invasive to the iris. The laser system may be set by the system to deliver laser light at a laser power that does not cause the temperature to exceed 140 C degrees during the color alteration procedure.

At step 740, process 700 (e.g., via one or more components of FIGS. 1-5) may deliver the laser light. For example, the system may (e.g., via control circuitry) deliver the laser light with the laser system (e.g., system 200 (FIG. 2)).

In some implementations, process 700 may include the system determining, as part of the color alteration procedure, stages of delivery of laser power to the iris such that successive stages cause removal of less pigment but are delivered at a higher laser power. The system may set setting the laser system to the laser power further based on a current stage of delivery and deliver the laser power based on the setting. There may be three stages and, in some embodiments, a first stage of the three stages delivers 26 times the MPE to the stromal pigment, a second stage of the three stages delivers 30 times the MPE to the stromal pigment, a third stage of the three stages delivers 34 times the MPE to the stromal pigment. The system may determine an immune response level of a patient based on accessing, by a control computer in communication with the laser system, a medical record of the patient containing data representative of the immune response level. The system may compare the immune response level to a range of immune responses associated with a time interval between two of the stages and reduce the time interval based on the comparing showing that the immune response level is higher than the range. The data may be representative of the immune response level quantifies the result of a pro-inflammatory cytokines test performed on the patient.

The above-described embodiments of the present disclosure are presented for purposes of illustration and not of limitation. Furthermore, it should be noted that the features and limitations described in any one embodiment may be applied to any other embodiment herein, and flowcharts or examples relating to one embodiment may be combined with any other embodiment in a suitable manner, done in different orders, or done in parallel. In addition, the systems and methods described herein may be performed in real time. It should also be noted that the systems and/or methods described above may be applied to, or used in accordance with, other systems and/or methods.

The present techniques will be better understood with reference to the following enumerated embodiments:

Embodiment 1: A method for altering an eye color of a patient with a color alteration procedure, the method comprising: tracking, with an optical tracking system, an eye of the patient during the color alteration procedure; determining a laser power to deliver to stromal pigment in an iris of the eye of the patient by at least retrieving a set of laser criteria for delivery of an exposure less than 100 times a maximum permissible exposure that causes elimination of at least a portion of the stromal pigment; setting a laser system to deliver laser light at the laser power which is less than the set of laser criteria; and delivering the laser light with the laser system.

Embodiment 2: The method of any of the preceding embodiments, wherein the elimination is caused by initiation of macrophagic digestion of the stromal pigment.

Embodiment 3: The method of any of the preceding embodiments, wherein the elimination is caused by ablation of the stromal pigment.

Embodiment 4: The method of any of the preceding embodiments, wherein the laser power is less than 75 times the maximum permissible exposure.

Embodiment 5: The method of any of the preceding embodiments, wherein the laser power is less than 50 times the maximum permissible exposure.

Embodiment 6: The method of any of the preceding embodiments, wherein the laser power is sufficient to cause a concurrent temperature change in the iris causing macrophages in the patient to remove at least a portion of the stromal pigment.

Embodiment 7: The method of any of the preceding embodiments, wherein the laser power is at least 20 times the maximum permissible exposure such that a reduction of the laser power below 20 times the maximum permissible exposure does not cause denaturation of the stromal pigment and the resultant macrophagic elimination and change in eye color.

Embodiment 8: The method of any of the preceding embodiments, further comprising: monitoring, with a temperature sensor, the temperature of at least a portion of the stromal pigment; and controlling the laser system to deliver the laser power such that the delivery raises the temperature to 115-125° C., inclusive, as monitored with the temperature sensor.

Embodiment 9: The method of any of the preceding embodiments, the monitoring comprising performing real-time imaging of the iris for detecting microbubbles.

Embodiment 10: The method of any of the preceding embodiments, the monitoring comprising performing real-time acoustical monitoring of the iris for detecting microbubbles.

Embodiment 11: The method of any of the preceding embodiments, further comprising: imaging the iris with an image sensor prior to the procedure to generate a plurality of images of the iris; analyzing the images with image processing software; generating, based on the image analyses, a mapping of the iris, the mapping comprising a plurality of regions corresponding to varying absorption coefficients of a treatment wavelength of the stromal pigment of the iris; and setting, based on the mapping, the laser system to deliver laser light at a first laser power to a location in the eye of the patient, wherein the first laser power is sufficient to cause elimination of at least a portion of stromal pigment in the iris.

Embodiment 12: The method of any of the preceding embodiments further comprising tracking, with an optical tracking system, an eye of the patient during the color alteration procedure.

Embodiment 13: The method of any of the preceding embodiments, the tracking comprising: capturing an image of the iris with the optical tracking system; comparing the image to a prior image of the iris to determine whether there has been a change in an iris position; and computing deltas for the change in position from the image and the prior image, wherein the delivery of the laser light is shifted based on the deltas.

Embodiment 14: The method of any of the preceding embodiments, wherein the optical tracking system includes a rangefinder, the method further comprising determining, utilizing the rangefinder, a distance between the iris and a reference component of the optical tracking system.

Embodiment 15: The method of any of the preceding embodiments, wherein the distance is determined with a resolution of at least 10 microns.

Embodiment 16: The method of any of the preceding embodiments, wherein the rangefinder is a time-domain optical coherence tomography system or a spectral domain optical coherence tomography system.

Embodiment 17: The method of any of the preceding embodiments, wherein the reference component is a last lens in the optical tracking system.

Embodiment 18: The method of any of the preceding embodiments, further comprising autofocusing the laser system in response to the distance.

Embodiment 19: The method of any of the preceding embodiments, the autofocusing comprising: measuring a distance to the stromal pigment of the iris at periodic intervals; and controlling, based on the distance, the laser system to remain substantially in focus between an anterior surface and posterior surface of the iris.

Embodiment 20: The method of any of the preceding embodiments, wherein the rangefinder comprises one or more of: triangulation lasers, time of flight detectors, phase shift detectors, ultrasonic detectors, frequency modulation detectors, interferometers, a camera, or a light sensor.

Embodiment 21: The method of any of the preceding embodiments, further comprising: determining, as part of the color alteration procedure, stages of delivery of laser power to the iris such that successive stages cause removal of less pigment but are delivered at a higher laser power; setting the laser system to the laser power further based on a current stage of delivery; and delivering the laser power based on the setting.

Embodiment 22: The method of any of the preceding embodiments, wherein the plurality of stages includes at least three stages.

Embodiment 23: The method of any of the preceding embodiments, wherein a first stage of the at least three stages delivers approximately 25.4-26.6 times the MPE to the stromal pigment, a second stage of the at least three stages delivers approximately 29.4-30.6 times the MPE to the stromal pigment, a third stage of the at least three stages delivers approximately 33.4-34.6 times the MPE to the stromal pigment.

Embodiment 24: The method of any of the preceding embodiments, further comprising: determining an immune response level of a patient based on accessing, by a control computer in communication with the laser system, a medical record of the patient containing data representative of the immune response level; comparing the immune response level to a range of immune responses associated with a time interval between two of the stages; and reducing the time interval based on the comparing showing that the immune response level is higher than the range.

Embodiment 25: The method of any of the preceding embodiments, wherein the data representative of the immune response level quantifies the result of a pro-inflammatory cytokines test performed on the patient.

Embodiment 26: A method for altering an eye color of a patient with a color alteration procedure, the method comprising: tracking, with an optical tracking system, an eye of the patient during the color alteration procedure; determining a spot size for laser light to be delivered to a stromal pigment of an iris of the eye of the patient by at least retrieving a set of laser criteria that result in delivery of laser light having a spot size of 4-70 microns, inclusive, to a stromal pigment of an iris of the patient; setting a laser system to deliver the laser light at the spot size; and delivering the laser light with the laser system.

Embodiment 27: The method of any of the preceding embodiments, wherein the spot size is between 10-40 microns, inclusive.

Embodiment 28: The method of any of the preceding embodiments, wherein the spot size is between 25-30 microns, inclusive.

Embodiment 29: The method of any of the preceding embodiments, wherein the laser power in combination with the spot size is sufficient to cause a concurrent temperature change in the iris causing initiation of macrophagic digestion of the stromal pigment.

Embodiment 30: The method of any of the preceding embodiments, further comprising: determining, with a temperature sensor, a temperature of at least a portion of the iris that contains stromal pigment, wherein the temperature sensor is non-invasive to the iris; and setting a laser system to deliver laser light at a laser power that does not cause the temperature to exceed 140 degrees during the color alteration procedure.

Embodiment 31: The method of any of the preceding embodiments, further comprising: imaging the iris with an image sensor prior to the procedure to generate a plurality of images of the iris; generating, based on the images, a mapping of the iris, the mapping comprising a plurality of regions corresponding to varying absorption coefficients of a treatment wavelength of the stromal pigment of the iris; and setting, based on the mapping, the laser system to deliver laser light at a first laser power to a location in the eye of the patient, wherein the first laser power is sufficient to cause elimination of at least a portion of stromal pigment in the iris.

Embodiment 32: The method of any of the preceding embodiments further comprising tracking, with an optical tracking system, an eye of the patient during the color alteration procedure.

Embodiment 33: The method of any of the preceding embodiments, wherein the optical tracking system includes a rangefinder, the method further comprising determining, utilizing the rangefinder, a distance between an iris of the eye and a reference component of the optical tracking system.

Embodiment 34: The method of any of the preceding embodiments, wherein the reference component is a last lens in the optical tracking system.

Embodiment 35: The method of any of the preceding embodiments, further comprising autofocusing the laser system in response to the distance.

Embodiment 36: The method of any of the preceding embodiments, the autofocusing comprising: measuring a distance to the stromal pigment of the iris at periodic intervals; and controlling, based on the distance, the laser system to remain substantially in focus at the stromal pigment.

Embodiment 37: The method of any of the preceding embodiments, wherein the rangefinder comprises one or more of: triangulation lasers, time of flight detectors, phase shift detectors, ultrasonic detectors, frequency modulation detectors, interferometers, a camera, or a light sensor.

Embodiment 38: The method of any of the preceding embodiments, further comprising: determining, as part of the color alteration procedure, stages of delivery of laser power to the iris such that successive stages cause removal of less pigment but are delivered at a higher laser power; setting the laser system to the laser power further based on a current stage of delivery; and delivering the laser power based on the setting.

Embodiment 39: The method of any of the preceding embodiments, wherein the plurality of stages includes at least three stages.

Embodiment 40: The method of any of the preceding embodiments, wherein a first stage of the at least three stages delivers 25.4-26.6 times the MPE to the stromal pigment, a second stage of the three stages delivers 29.4-30.6 times the MPE to the stromal pigment, a third stage of the at least three stages delivers 33.4-34.6 times the MPE to the stromal pigment.

Embodiment 41: The method of any of the preceding embodiments, further comprising: determining an immune response level of a patient based on accessing, by a control computer in communication with the laser system, a medical record of the patient containing data representative of the immune response level; comparing the immune response level to a range of immune responses associated with a time interval between two of the stages; and reducing the time interval based on the comparing showing that the immune response of the patient is higher than the range.

Embodiment 42: The method of any of the preceding embodiments, wherein the data representative of the immune response level quantifies a result of a pro-inflammatory cytokines test performed on the patient.

Embodiment 43: A tangible, non-transitory, machine-readable medium storing instructions that, when executed by a data processing apparatus, cause the data processing apparatus to perform operations comprising those of any of the above method embodiments 1-42.

Embodiment 44: A system comprising: one or more processors; and memory storing instructions that, when executed by the processors, cause the processors to effectuate operations comprising those of any of the above method embodiments 1-42.

Appendix 1—Thermal Hazard Weighting Functions

| Wavelength (nm) | Thermal hazard weighting function $R(\lambda)$ |
| --- | --- |
| 305 | 2.19 |
| 310 | 2.31 |
| 315 | 2.42 |
| 320 | 2.53 |
| 325 | 2.63 |
| 330 | 2.72 |
| 335 | 2.80 |
| 340 | 2.87 |
| 345 | 2.94 |
| 350 | 2.99 |
| 355 | 3.04 |
| 360 | 3.08 |
| 365 | 3.11 |
| 370 | 3.14 |
| 375 | 3.16 |
| 380 | 3.17 |
| 385 | 3.17 |
| 390 | 3.17 |
| 395 | 3.17 |
| 400 | 3.16 |
| 405 | 3.14 |
| 410 | 3.12 |
| 415 | 3.10 |
| 420 | 3.07 |
| 425 | 3.04 |
| 430 | 3.01 |
| 435 | 2.97 |
| 440 | 2.93 |
| 445 | 2.89 |
| 450 | 2.85 |
| 455 | 2.81 |
| 460 | 2.76 |
| 465 | 2.72 |
| 470 | 2.67 |
| 475 | 2.63 |
| 480 | 2.58 |
| 485 | 2.53 |
| 490 | 2.48 |
| 495 | 2.44 |
| 500 | 2.39 |
| 505 | 2.34 |
| 510 | 2.30 |
| 515 | 2.25 |
| 520 | 2.20 |
| 525 | 2.16 |
| 530 | 2.11 |
| 535 | 2.07 |
| 540 | 2.03 |
| 545 | 1.98 |
| 550 | 1.94 |
| 555 | 1.90 |
| 560 | 1.86 |
| 565 | 1.82 |
| 570 | 1.78 |
| 575 | 1.74 |
| 580 | 1.70 |
| 585 | 1.66 |
| 590 | 1.63 |
| 595 | 1.59 |
| 600 | 1.55 |
| 605 | 1.52 |
| 610 | 1.49 |
| 615 | 1.45 |
| 620 | 1.42 |
| 625 | 1.39 |
| 630 | 1.36 |
| 635 | 1.33 |
| 640 | 1.30 |
| 645 | 1.27 |
| 650 | 1.24 |
| 655 | 1.22 |
| 660 | 1.19 |
| 665 | 1.16 |
| 670 | 1.14 |
| 675 | 1.11 |
| 680 | 1.09 |
| 685 | 1.07 |
| 690 | 1.04 |
| 695 | 1.02 |
| 700 | 1.00 |
| 705 | 0.98 |
| 710 | 0.96 |
| 715 | 0.94 |
| 720 | 0.92 |
| 725 | 0.90 |
| 730 | 0.88 |

| Wavelength (nm) | Thermal hazard weighting function R(λ) |
|---|---|
| 735 | 0.86 |
| 740 | 0.84 |
| 745 | 0.83 |
| 750 | 0.81 |
| 755 | 0.79 |
| 760 | 0.78 |
| 765 | 0.76 |
| 770 | 0.74 |
| 775 | 0.73 |
| 780 | 0.71 |
| 785 | 0.70 |
| 790 | 0.69 |
| 795 | 0.67 |
| 800 | 0.66 |
| 805 | 0.65 |
| 810 | 0.63 |
| 815 | 0.62 |
| 820 | 0.61 |
| 825 | 0.60 |
| 830 | 0.59 |
| 835 | 0.57 |
| 840 | 0.56 |
| 845 | 0.55 |
| 850 | 0.54 |
| 855 | 0.53 |
| 860 | 0.51 |
| 865 | 0.50 |
| 870 | 0.49 |
| 875 | 0.47 |
| 880 | 0.47 |
| 885 | 0.46 |
| 890 | 0.44 |
| 895 | 0.43 |
| 900 | 0.42 |
| 905 | 0.41 |
| 910 | 0.40 |
| 915 | 0.38 |
| 920 | 0.35 |
| 925 | 0.32 |
| 930 | 0.29 |
| 935 | 0.26 |
| 940 | 0.23 |
| 945 | 0.19 |
| 950 | 0.16 |
| 955 | 0.15 |
| 960 | 0.15 |
| 965 | 0.14 |
| 970 | 0.13 |
| 975 | 0.13 |
| 980 | 0.13 |
| 985 | 0.13 |
| 990 | 0.13 |
| 995 | 0.14 |
| 1000 | 0.15 |
| 1005 | 0.15 |
| 1010 | 0.16 |
| 1015 | 0.16 |
| 1020 | 0.17 |
| 1025 | 0.18 |
| 1030 | 0.19 |
| 1035 | 0.20 |
| 1040 | 0.21 |
| 1045 | 0.21 |
| 1050 | 0.22 |
| 1055 | 0.22 |
| 1060 | 0.21 |
| 1065 | 0.21 |
| 1070 | 0.20 |
| 1075 | 0.20 |
| 1080 | 0.20 |
| 1085 | 0.20 |
| 1090 | 0.20 |
| 1095 | 0.19 |
| 1100 | 0.17 |
| 1105 | 0.14 |
| 1110 | 0.11 |
| 1115 | 0.084 |
| 1120 | 0.068 |
| 1125 | 0.059 |
| 1130 | 0.054 |
| 1135 | 0.050 |
| 1140 | 0.046 |
| 1145 | 0.040 |
| 1150 | 0.034 |
| 1155 | 0.029 |
| 1160 | 0.025 |
| 1165 | 0.021 |
| 1170 | 0.019 |
| 1175 | 0.017 |
| 1180 | 0.016 |
| 1185 | 0.016 |
| 1190 | 0.015 |
| 1195 | 0.015 |
| 1200 | 0.015 |
| 1205 | 0.016 |
| 1210 | 0.016 |
| 1215 | 0.017 |
| 1220 | 0.018 |
| 1225 | 0.019 |
| 1230 | 0.019 |
| 1235 | 0.020 |
| 1240 | 0.020 |
| 1245 | 0.020 |
| 1250 | 0.020 |
| 1255 | 0.019 |
| 1260 | 0.019 |
| 1265 | 0.018 |
| 1270 | 0.017 |
| 1275 | 0.015 |
| 1280 | 0.014 |
| 1285 | 0.013 |
| 1290 | 0.012 |
| 1295 | 0.011 |
| 1300 | 0.010 |
| 1305 | 0.009 |
| 1310 | 0.007 |
| 1315 | 0.006 |
| 1320 | 0.005 |
| 1325 | 0.004 |
| 1330 | 0.003 |
| 1335 | 0.002 |
| 1340 | 0.002 |
| 1345 | 0.001 |
| 1350 | 0.001 |

What is claimed is:

1. A method for altering an eye color of a patient with a color alteration procedure, the method comprising:
   determining a laser power to deliver to stromal pigment in an iris of the eye of the patient by at least retrieving a set of laser criteria for delivery of an exposure less than 100 times a maximum permissible exposure that causes elimination of at least a portion of the stromal pigment;
   setting a laser system to deliver laser light at the laser power which is less than the set of laser criteria;
   monitoring, with a temperature sensor, the temperature of at least a portion of the stromal pigment;
   controlling the laser system to deliver the laser power such that the delivery raises the temperature to 115-125° C., inclusive, as monitored with the temperature sensor; and
   delivering the laser light with the laser system.

2. The method of claim 1, wherein the elimination is caused by initiation of macrophagic digestion of the stromal pigment or the elimination is caused by ablation of the stromal pigment.

3. The method of claim 1, wherein the laser power is less than 75 times the maximum permissible exposure.

4. The method of claim 1, wherein the laser power is at least 20 times the maximum permissible exposure such that a reduction of the laser power below 20 times the maximum permissible exposure does not cause denaturation of the stromal pigment and the resultant macrophagic elimination and change in eye color.

5. The method of claim 1, the monitoring comprising performing real-time imaging of the iris for detecting microbubbles or performing real-time acoustical monitoring of the iris for detecting microbubbles.

6. The method of claim 1, further comprising:
imaging the iris with an image sensor prior to the procedure to generate a plurality of images of the iris;
analyzing the images with image processing software;
generating, based on the image analysis, a mapping of the iris, the mapping comprising a plurality of regions corresponding to varying absorption coefficients of a treatment wavelength of the stromal pigment of the iris; and
setting, based on the mapping, the laser system to deliver laser light at a first laser power to a location in the eye of the patient, wherein the first laser power is sufficient to cause elimination of at least a portion of stromal pigment in the iris.

7. The method of claim 1, further comprising tracking, with an optical tracking system, an eye of the patient during the color alteration procedure.

8. The method of claim 7, the tracking comprising:
capturing an image of the iris with the optical tracking system;
comparing the image to a prior image of the iris to determine whether there has been a change in an iris position; and
computing deltas for the change in position from the image and the prior image,
wherein the delivery of the laser light is shifted based on the deltas.

9. The method of claim 7, wherein the optical tracking system includes a rangefinder, the method further comprising determining, utilizing the rangefinder, a distance between the iris and a reference component of the optical tracking system.

10. The method of claim 9, wherein the distance is determined with a resolution of at least 10 microns.

11. The method of claim 9, wherein the rangefinder is a time-domain optical coherence tomography system or a spectral domain optical coherence tomography system or comprises one or more of: triangulation lasers, time of flight detectors, phase shift detectors, ultrasonic detectors, frequency modulation detectors, interferometers, a camera, or a light sensor.

12. The method of claim 9, further comprising autofocusing the laser system in response to the distance.

13. The method of claim 12, the autofocusing comprising:
measuring a distance to the stromal pigment of the iris at periodic intervals; and
controlling, based on the distance, the laser system to remain substantially in focus between an anterior surface and posterior surface of the iris.

14. The method of claim 1, further comprising:
determining, as part of the color alteration procedure, stages of delivery of laser power to the iris such that successive stages cause removal of less pigment but are delivered at a higher laser power;
setting the laser system to the laser power further based on a current stage of delivery; and
delivering the laser power based on the setting.

15. The method of claim 14, wherein the plurality of stages includes at least three stages.

16. The method of claim 14, further comprising:
determining an immune response level of a patient based on accessing, by a control computer in communication with the laser system, a medical record of the patient containing data representative of the immune response level;
comparing the immune response level to a range of immune responses associated with a time interval between two of the stages; and
reducing the time interval based on the comparing showing that the immune response level is higher than the range.

17. A method for altering an eye color of a patient with a color alteration procedure, the method comprising:
determining a spot size for laser light to be delivered to a stromal pigment of an iris of the eye of the patient by at least retrieving a set of laser criteria that result in delivery of laser light having a spot size of 4-70 mm, inclusive, to a stromal pigment of an iris of the patient;
setting a laser system to deliver the laser light at the spot size;
determining, with a temperature sensor, a temperature of at least a portion of the iris that contains stromal pigment, wherein the temperature sensor is non-invasive to the iris; and
setting a laser system to deliver laser light at a laser power that raises the temperature to 115-125° C., inclusive, during the color alteration procedure; and
delivering the laser light with the laser system.

18. The method of claim 17, wherein the laser power in combination with the spot size is sufficient to cause a concurrent temperature change in the iris causing initiation of macrophagic digestion of the stromal pigment.

19. The method of claim 17, further comprising:
imaging the iris with an image sensor prior to the procedure to generate a plurality of images of the iris;
generating, based on the images, a mapping of the iris, the mapping comprising a plurality of regions corresponding to varying absorption coefficients of a treatment wavelength of the stromal pigment of the iris; and
setting, based on the mapping, the laser system to deliver laser light at a first laser power to a location in the eye of the patient, wherein the first laser power is sufficient to cause elimination of at least a portion of stromal pigment in the iris.

20. The method of claim 17, further comprising tracking, with an optical tracking system, an eye of the patient during the color alteration procedure.

21. The method of claim 20, wherein the optical tracking system includes a rangefinder, the method further comprising determining, utilizing the rangefinder, a distance between an iris of the eye and a reference component of the optical tracking system.

22. The method of claim 20, further comprising autofocusing the laser system in response to the distance.

23. The method of claim 22, the autofocusing comprising:
measuring a distance to the stromal pigment of the iris at periodic intervals; and
controlling, based on the distance, the laser system to remain substantially in focus at the stromal pigment.

24. The method of claim 17, further comprising:
determining, as part of the color alteration procedure, stages of delivery of laser power to the iris such that successive stages cause removal of less pigment but are delivered at a higher laser power;
setting the laser system to the laser power further based on a current stage of delivery; and
delivering the laser power based on the setting.

25. The method of claim 24, wherein the plurality of stages includes at least three stages.

26. The method of claim 24, further comprising:
determining an immune response level of a patient based on accessing, by a control computer in communication with the laser system, a medical record of the patient containing data representative of the immune response level;
comparing the immune response level to a range of immune responses associated with a time interval between two of the stages; and
reducing the time interval based on the comparing showing that the immune response of the patient is higher than the range.

\* \* \* \* \*